US009676948B2

(12) United States Patent
Hwang

(10) Patent No.: US 9,676,948 B2
(45) Date of Patent: Jun. 13, 2017

(54) COATING COMPOSITION AND METHOD FOR DETERMINING THE UNIFORMITY AND THICKNESS OF A NO-RINSE SILANE PRETREATMENT

(71) Applicant: Momentive Performance Materials Inc., Waterford, NY (US)

(72) Inventor: Lesley Hwang, Chappaqua, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 461 days.

(21) Appl. No.: 14/223,424

(22) Filed: Mar. 24, 2014

(65) Prior Publication Data

US 2014/0342164 A1 Nov. 20, 2014

Related U.S. Application Data

(60) Provisional application No. 61/805,248, filed on Mar. 26, 2013.

(51) Int. Cl.

| C09D 7/00 | (2006.01) |
|---|---|
| B05D 7/14 | (2006.01) |
| B05D 3/00 | (2006.01) |
| G01N 23/223 | (2006.01) |
| G01B 11/06 | (2006.01) |
| C09D 183/08 | (2006.01) |
| C08K 5/5455 | (2006.01) |

(52) U.S. Cl.
CPC ............ *C09D 7/007* (2013.01); *B05D 3/007* (2013.01); *B05D 7/14* (2013.01); *C09D 183/08* (2013.01); *G01B 11/0616* (2013.01); *G01B 11/0658* (2013.01); *G01N 23/223* (2013.01); *C08K 5/5455* (2013.01); *Y10T 428/31663* (2015.04)

(58) Field of Classification Search
CPC ...................................................... C09D 7/007
See application file for complete search history.

(56) References Cited

U.S. PATENT DOCUMENTS

| 3,940,417 A | 2/1976 | Schlaepfer |
| 4,009,994 A | 3/1977 | Schlaepfer |
| 4,146,725 A | 3/1979 | Meyer et al. |
| 4,250,317 A | 2/1981 | Meyer et al. |
| 4,271,293 A | 6/1981 | Bremen |
| 4,360,679 A | 11/1982 | Meyer et al. |
| 4,542,222 A | 9/1985 | Meyer et al. |
| 4,609,738 A | 9/1986 | Mockli |

| 2006/0228470 A1 | 10/2006 | He et al. |
| 2007/0090329 A1 | 4/2007 | Su et al. |
| 2008/0245260 A1 | 10/2008 | Campazzi et al. |
| 2010/0178521 A1 | 7/2010 | Byrne et al. |
| 2013/0295292 A1* | 11/2013 | Bukeikhanova ......... C09D 5/08 427/420 |

FOREIGN PATENT DOCUMENTS

| EP | 1240258 B1 | 11/2005 | |
| GB | 1279317 A * | 6/1972 | ............ C09B 23/06 |
| WO | 2008055890 A1 | 5/2008 | |
| WO | WO 2012055908 A1 * | 5/2012 | ............... C09D 5/08 |

OTHER PUBLICATIONS

"Malachite Green", The Dictionary of Substances and Their Effects, 2005, The Royal Society of Chemistry/Knovel Corp, 2 pages.*
Valley 885 et al., "Basic Dye", (Sep. 4, 2011), XP055126308, Retrieved from the Internet: URL:http://www.americandyestuff.com/products/print/basic-dyes-for-textiles-and-paper.pdf [retrieved on Jul. 2, 2014] the whole document.
Christie R M ED—Clark (ED) M: "Fluorescent dyes", (Jan. 1, 2011), Handbook of Textile and Industrial Dyeing: [Woodhead Publishing Series in Textiles], WP Woodhead Publ., UK, pp. 562-587, XP008170273 [retrieved on Jan. 30, 2014].
Gao J.C. et al., "Characteristics and Properties of Surface Coated nano-Ti02", Transactions of Nonferrous Metals Society of China, vol. 16, No. 6. Dec. 1, 2006, pp. 1252-1258, XP022936050, ISSN: 1003-5326, DOI: 10.1016/S1003-6326(07)60002-8 [retrieved on Dec. 1, 2006] abstract.
Gharaibeh et al., "Fluorescence emission sensing in coatings: Method for defects detection in coated surfaces of structural elements", Progress in Organic Coatings, Elsevier BV, NL, vol. 58, No. 4, (Mar. 8, 2007), pp. 282-289,XP005917735, ISN: 0300-9440, DOI: 10.1016/J. Porgcoat. 2006.12.005 the whole document.
International Search Report and Written Opinion of the International Searching Authority dated Jul. 10, 2014.
Masters Thesis of Vignesh Morudhanayagom Palanivel, University of Cincinnati, Jul. 25, 2003, "Modified silane thin films as an alternative to chromates for corrosion protection of AA2024-T3 alloy".

* cited by examiner

*Primary Examiner* — Nicole M Buie-Hatcher
(74) *Attorney, Agent, or Firm* — James C. Abruzzo

(57) ABSTRACT

The invention is directed to a detectable and stable composition comprising an organofunctional silane and/or hydrolyzate and/or partial or complete condensate thereof, a colloidal metal oxide, a water soluble organic dye having a positive charge and a counterion derived from a carboxylic acid of from 1 to 6 carbon atoms, and water. The invention is also directed to a method for determining the uniformity and film thickness of a detectable composition applied to a substrate comprising applying to the surface of the substrate the detectable composition and measuring an optical property of the applied coating, the resulting measurement being related to the uniformity of the applied composition.

18 Claims, 1 Drawing Sheet

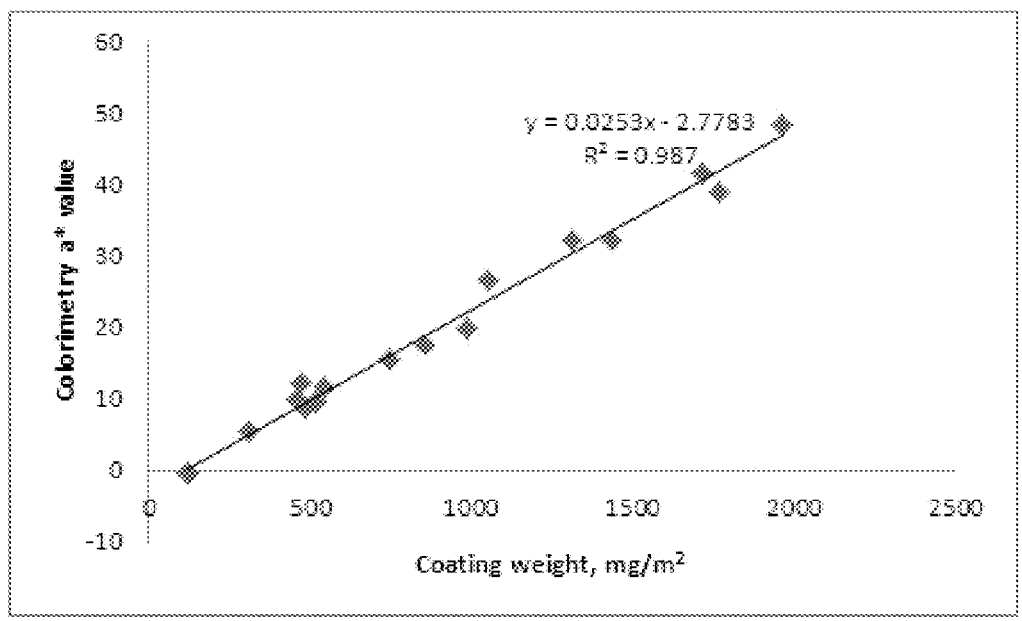

COATING COMPOSITION AND METHOD FOR DETERMINING THE UNIFORMITY AND THICKNESS OF A NO-RINSE SILANE PRETREATMENT

This application claims priority to Provisional U.S. Patent Application No. 61/805,248, filed Mar. 26, 2013, the entire contents of which are incorporated herein by reference in its entirety.

FIELD OF INVENTION

The invention relates to a coating composition for metals. Particularly, the invention relates to a no-rinse, non-chromate, non-metal phosphate coating for metal substrates, especially steel, zinc coated steel, and aluminum surfaces wherein the coating comprises a water soluble organic dye to provide a means for determining the uniformity and thickness of the coating on the surface.

BACKGROUND OF THE INVENTION

A variety of commercial coating compositions are known for preparing metal surfaces to prevent corrosion and improve adhesion of paints or other coatings to the surface. For example, silane pretreatment coatings are used in commercial applications to provide anticorrosion properties to metal surfaces and/or to prepare the metal surfaces prior to painting operations. However, silane pretreatments are colorless when applied, are applied at very low coating weights, and are extremely difficult to detect by human visual inspection.

Methods for determining the presence of thin films on a substrate are known. Certain fluorescent dyes in metal film coatings have been used to determine whether or not the coating has been applied to the surface. Specifically, the fluorescent brightening agents stilbene and coumarin are added to a chrome-free metal coating and, after coating the metal with the coating, the metal is viewed under ultraviolet (UV) light and the presence of coating is detected by eye. The methods are useful in their ability to determine whether a coating has been applied to a substrate. The methods have been developed which involve quantitative determination of the thickness of the coating, an important quality control matter. Although possible, use of stilbene and coumarin in quantitative determinations of thickness of a coating is not preferred because it has been found that these compounds often do not display the required precision in their use in a calibrated system to determine coating thickness that is required in a commercially feasible coating thickness measurement system. The native fluorescence of the coating can interfere with measurement of fluorescent intensity of the coating.

Methods for determining thickness of transparent oil films on metal surfaces by detection of fluorescent compounds mixed in the oil are also known. However, due to the nature of oil films, these methods are not precise and, therefore, are not suitably reproducible for determination of the thickness of a dryable, dried, curable or cured film-forming coating on a substrate. Choice of dye is not important when the dye is used to measure oil film thickness. The layer of oil is typically not maintained on the surface of the substrate if additional layers of a coating are needed on the oil-covered substrate, such as a pre-coating a primer or a color coat.

Many of the organic dyes of the prior art are not readily soluble in waterborne pretreatments and thus, often affect the stability of the pretreatment. Addition of these organic dyes results in precipitation or gelation of the other components of the pretreatment, thereby making the pretreatment composition unstable. The poor shelf-life of the pretreatment affects the usability of these pretreatments because the precipitation or gelation results in non-uniform coating or the formation of voids or poorly coated surfaces. Poor corrosion resistance and poor adhesion of paints or other coatings to the metal substrate result when these unstable pretreatments are used. Accordingly, there is a need to be able to quickly detect the presence, uniformity and thickness of these pretreatments as an essential aspect of quality control.

SUMMARY OF THE INVENTION

The present invention pertains to a composition for coating the surfaces of a metal substrate, such as steel, zinc coated steels, and aluminum, to provide for the formation of a coating which is detectable, quantifiable and also increases the corrosion resistance of the substrate and/or the adhesion properties of the substrate.

In one embodiment herein there is provided a detectable coating composition comprising:
(a) organofunctional silane and/or hydrolyzate and/or partial or complete condensate thereof;
(b) colloidal metal oxide;
(c) water soluble organic dye having a positive charge and a counterion derived from a carboxylic acid containing from 1 to about 6 carbon atoms; and,
(d) water,
wherein said composition does not contain detrimental amounts of precipitates for a period of at least 48 hours when stored at 25° C.

The methods of the invention comprise applying the coating composition to a surface of the requisite substrate and then determining the uniformity of the coating.

In one embodiment herein there is also provided a method of determining the uniformity of a coating composition applied to a substrate comprising applying to a surface of a substrate a coating composition comprising:
(a) organofunctional silane and/or hydrolyzate and/or partial or complete condensate thereof;
(b) colloidal metal oxide;
(c) water soluble organic dye having a positive charge and a counterion derived from a carboxylic acid containing from 1 to about 6 carbon atoms; and,
(d) water, wherein said composition does not contain detrimental amounts of precipitates for a period of at least 48 hours when stored at 25° C.; and, measuring an optical property of the applied coating, the resulting measurement being related to the uniformity of the applied coating.

BRIEF DESCRIPTION OF THE DRAWING

FIG. 1 is a plot of the a* values for Coating A to E versus the coating weights on HDG substrate.

DETAILED DESCRIPTION OF THE INVENTION

In accordance with the invention, it has been discovered that detectable compositions, specifically, chrome-free, and more specifically phosphate-free detectable pretreatment coatings, are provided on a substrate by contacting the desired surface with said composition containing an aqueous, water soluble organic dye. The substrate includes electrogalvanized steel, cold rolled steel, hot dip galvanized steel, aluminum, and other metals. Specifically, the water soluble organic dye has a positive charge and a counterion derived from a carboxylic acid containing from 1 to about 6 carbon atoms.

The detectable composition comprises an organofunctional silane and/or hydrolyzate and/or partial or complete condensate thereof. The stabilized suspension further comprises a colloidal metal oxide. Specifically, the metal oxide includes silica and/or cerium oxide particles. In a more specific aspect of the invention, stabilizing agent(s) is/are added to the detectable composition to enhance product stability and shelf life. The detectable compositions include aqueous pretreatments, specially conversion coatings and passivation coatings. Aqueous detectable pretreatment compositions of the invention provide improved corrosion resistance of bare and painted metal, and adhesion of applied coatings to painted metal. In the context of the invention, the term "bare metal" refers to metal surfaces that are treated with the conversion or passivation coating of the invention but which have not been painted.

In one specific embodiment herein, it will be understood that all ranges herein comprise can comprise all ranges therebetween, and any combination of endpoints of said ranges and/or subranges thereof.

The expression "detectable coating composition" as used herein comprises the organofunctional silanes (a) and/or hydrolyzates and/or condensates thereof, the colloidal metal oxide (b), water soluble organic dye having a positive charge and a counterion derived from a carboxylic acid containing from 1 to about 6 carbon atoms (c); water (d), optional stabilizing agent (e), optional adjuvant (f) and optional pH adjusting agents (g), wherein said composition does not contain detrimental amounts of precipitates for a period of at least 48 hours when stored at 25° C.

In one embodiment herein there is provided a detectable coating composition comprising;
  (a) silicon-containing compound selected from the group consisting of organofunctional silane, a hydrolyzate of said organofunctional silane, a condensate of the said organofunctional silane and mixtures thereof in the amount of 0.01 to 80 weight percent, wherein the organofunctional silane (a) is of the general formula (I):

wherein X is an organofunctional group of valence r, including mono-, di-, or polyvalent groups, wherein each occurrence of $R^1$ is independently a linear, branched or cyclic divalent organic group containing up to about 12 carbon atoms, and optionally containing one or more heteroatoms, with the proviso that X and the silicon atom of the silyl group are bonded to the $R^1$ group through a covalent bond to a carbon atom of $R^1$, thereby forming a bridge between organofunctional group X and the silyl group; each occurrence of $R^2$ independently is alkyl, alkoxy-substituted alkyl, aryl, or aralkyl, all containing up to about 16 carbon atoms, each $R^3$ independently is acetyl, alkyl, or alkoxy-substituted alkyl, all containing up to about 16 carbon atoms, or hydrogen; X is an organofunctional group of valence r, including mono-, di- or polyvalent functional groups, r is an integer of from 1 to 4; and a is 0, 1 or 2;

(b) water soluble organic dye having a positive charge and a counterion derived from a carboxylic acid containing from 1 to about 6 carbon atoms in an amount of from 0.0001 to about 5 weight percent and having the structure of formula (IV)

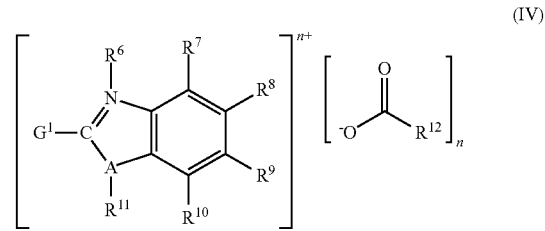

wherein:
  $G^1$ is an organic group having from 1 to about 20 carbon atoms and containing at least one oxygen or nitrogen heteroatom;
  A is a nitrogen atom or $(-)_3C-R^*$, where $R^*$ is a monovalent group chosen from alkyl, cycloalkyl, alkenyl, aralkyl or aryl group each having up to about 10 carbon atoms;
  $R^6$ is an alkyl, a hydroxylalkyl, an alkoxyalkyl, a cycloalkyl, an aralkyl optionally substituted with a halogen or alkoxy group, an aryl optionally substituted with a halogen or alkoxy group, a cyanoalkyl, a carbamatoalkyl or a carboalkoxyalkyl group containing up to about 10 carbon atoms, or hydrogen;
  $R^7$ is an alkyl, alkoxy, aryl alkylsulfonyl, or arylsulfonyl group containing up to about 10 carbon atoms or hydrogen;
  $R^8$ is an alkyl, alkoxy, aryl alkylsulfonyl, arylsulfonyl, or aminosulfonyl group containing up to about 10 carbon atoms or hydrogen;
  $R^9$ is an alkyl, alkoxy, aryl alkylsulfonyl, or arylsulfonyl group containing up to about 10 carbon atoms or hydrogen;
  $R^{10}$ is an alkyl, alkoxy, aryl alkylsulfonyl, or arylsulfonyl group containing up to about 10 carbon atoms or hydrogen;
  $R^{11}$ is an alkyl, a hydroxylalkyl, an alkoxyalkyl, cycloalkyl, an aralkyl optionally substituted with a halogen or alkoxy group, an aryl optionally substituted with a halogen or alkoxy group, a cyanoalkyl, a carbamatoalkyl or an alkoxycarbonylalkyl group containing up to about 10 carbon atoms or hydrogen,
  $R^{12}$ is an alkyl group containing from 1 to about 6 carbon atoms or hydrogen; and
  n is an integer of from 1 to 3;
or (VII)

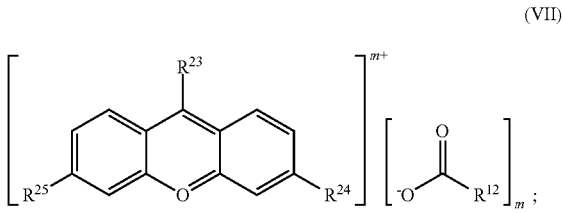

wherein:
R$^{12}$ is an alkyl group containing from 1 to about 6 carbon atoms or hydrogen;
R$^{23}$ is hydrogen, an alkyl group of from 1 to about 6 carbon atoms, an aryl group of from 6 to about 10 carbon atoms, an aralkyl group of from 7 to about 12 carbon atoms or an aryl group of from 6 to about 12 carbon atoms substituted with a hydroxycarbonyl group (—C(=O)OH) or substituted with an alkoxycarbonyl group —C(=O)OR$^{26}$, where R$^{26}$ is an alkyl group of from 1 to about 4 carbon atoms;
R$^{24}$ is hydrogen, an alkyl group containing 1 to about 6 carbon atoms, hydroxyl or amino having the structure —NR$^{27}$R$^{28}$, where R$^{27}$ and R$^{28}$ are each independently a hydrogen or alkyl group of from 1 to about 6 carbon atoms;
R$^{25}$ is hydrogen, an alkyl group containing 1 to about 6 carbon atoms, hydroxyl or amino having the structure —NR$^{27}$R$^{28}$, where R$^{27}$ and R$^{28}$ are each independently a hydrogen or alkyl group of from 1 to about 6 carbon atoms; and
m is an integer from 1 to 3;
(c) water in the amount of from 18 to 98 weight percent; and, optionally,
(d) stabilizing agent in the amount of about 1 to about 20 weight percent, wherein the weight of the silicon-containing compounds is the sum of the weights of the organofunctional silane component, the hydrolyzate of said organofunctional silane component and the condensate of the said organofunctional silane and the percents by weight are based upon the total weight of the composition and wherein said composition does not contain detrimental amounts of precipitates for a period of at least 48 hours when stored at 25° C.

The expression "stable suspension" as used herein comprises a suspension exhibiting little or no change in physical appearance, such as visible sedimentation or gelling for a period of at least 2 days of continuous, undisturbed storage at a temperature of from 10 to 70° C., and more specifically, at a temperature of from 15 to 35° C. It will be understood herein that in one embodiment, the stable suspension can be the detectable composition itself without the addition of other components, or alternatively, the stable suspension can be the detectable composition itself with the addition of optional additional components, such as the non-limiting examples of stabilizing agent and the like. In one non-limiting embodiment herein it will be understood that the expressions "detectable composition", "coating composition" or "composition" are used interchangeably with the expression "stable suspension" or the term "suspension". It will be understood herein that the ranges of amounts of various components described herein are based on the total weight of the detectable composition.

The expression "detectable composition" as used herein comprises a composition in which its presence of the composition can be determined on the surface of a substrate when applied at amounts equal to or greater than 5 mg/m$^2$ using an optical method. Optical methods are any method using a light sensitive device. In one embodiment, light sensitive devices are colorimeter, photoluminescent devices such as fluorescent detector and phosphorescent detector in which the substrate containing said composition is irradiated with radiant energy, which excites the organic dye to a higher electronic state and the emits excess energy to return to the ground electronic state, and the human eye.

The expression "detrimental amounts of precipitates" as used herein comprises the formation of solids or liquids which do not form a stable suspension as described herein. Detrimental amounts of precipitate are amounts greater than about 1000 milligram of precipitate per kilogram of the detectable composition, more specifically amount greater than about 100 milligram of precipitate per kilogram of the detectable composition and even more specifically greater than about 10 milligram of precipitate per kilogram of the detectable composition. In one embodiment, the amount of precipitate is determined gravimetrically. The gravimetric method involves filtering one kilogram of the detectable composition through a dried, pre-weighed absorbent filter pad with a pore size of 1 micron, drying said pad in an oven for 1 hour at 110° C. and measuring the weight gain. The difference between the pre-dried filter pad and the weight of the filter pad after filtration and drying is the amount of precipitate.

The detectable composition herein comprises one or more organofunctional silanes or a hydrolyzate and/or partial or complete condensate thereof, such as the non-limiting example of ureidosilanes.

In one embodiment herein the phrase "organofunctional silane" is understood to be any alkoxysilane and/or acyloxysilane that in addition to its alkoxy or acyloxy functionality the silane has an additional organic functionality.

In one embodiment herein, it will be understood that ureidoalkoxysilane is a more specific embodiment of an organofunctional silane, which can be used in any embodiment herein. In one embodiment herein, in any of the compositions and/or methods described herein, ureidosilane can be, in one non-limiting embodiment, an organofunctional silane.

In one embodiment an organofunctional silane is an alkoxysilane and/or acyloxysilane that can be hydrolyzed with any water, specifically water present in any compositions and/or methods described herein to yield the presence of hydrolyzate and/or partial or complete condensate thereof in said compositions and/or methods. In yet another embodiment a hydrolyzate is the partial and/or completely hydrolyzed product of organofunctional silane. In another further embodiment, similar to the hydrolysis of organofunctional silane described herein, hydrolyzate can be subject to a condensation reaction that can involve condensation reactions known to those skilled in the art that can yield partially and/or completely condensed hydrolyzates. In another embodiment herein, the level of hydrolysis of the herein described organofunctional silane can be the amount that occurs instantly upon exposure of the silane to moisture up to complete hydrolysis of the organofunctional silane.

In one embodiment herein, organofunctional silane (a) is of the general formula (I):

wherein X
is an organofunctional group of valence r, including mono-, di- or, polyvalent groups, wherein each occurrence of R$^1$ is independently a linear, branched or cyclic divalent organic group of up to 12 carbon atoms, more specifically up to about 10 carbon atoms, and most specifically from up to about 8 carbon atoms and optionally containing one or more heteroatoms, such as the non-limiting examples of O, N, P, Cl, Br, I and S, with the proviso that X and the silicon atom of the silyl group are bonded to the R¹ group through a covalent bond to a carbon atom of R¹, thereby forming a bridge between organofunctional group X and the silyl group; each occurrence of R² independently is alkyl, alkoxy-substituted alkyl, aryl, or aralkyl, each containing up to 16 carbon atoms, more specifically from up to about 12 carbon atoms and most specifically from up to about 8 carbon atoms, each R³ independently is acetyl, alkyl, or alkoxy-substituted alkyl, all each containing up to about 16 carbon atoms, more specifically up to about 12 carbon atoms and most specifically up to about 8 carbon atoms or hydrogen; r is an integer of from 1 to 4, more specifically 1 or 2 and most specifically 1; and a is 0, 1 or 2, more specifically 0 or 1 and most specifically 0.

Non-limiting examples of R¹ are methylene, ethylene, propylene, isopropylene, butylene, isobutylene, cyclohexylene, arylene and alkarylene groups.

In one embodiment X is a functional group, such as the non-limiting examples of mercapto, acyloxy, glycidoxy, epoxy, epoxycyclohexyl, epoxycyclohexylethyl, hydroxy, episulfide, acrylate, methacrylate, ureido, thioureido, vinyl, allyl, thiocarbamate, dithiocarbamate, ether, thioether, disulfide, trisulfide, tetrasulfide, pentasulfide, hexasulfide, polysulfide, xanthate, trithiocarbonate, dithiocarbonate, cyanurato, isocyanurato, —NHC(=O)OR⁵ or —NHC(=O)SR⁵ where R⁵ is a monovalent hydrocarbyl group containing from 1 to 12 carbon atoms, more specifically from 1 to 8 carbon atoms or another —Si(R²)$_a$(OR³)$_{3-a}$ group wherein R², R³ and a are as defined.

In one embodiment the set of univalent organofunctional groups herein includes, but is not limited to, mercapto; acyloxy, such as acryloxy, methacryloxy, and acetoxy; glycidoxy, —O—CH₂—C₂H₃O; epoxycyclohexylethyl, —CH₂—CH₂—C₆H₉O; epoxycyclohexyl, —C₆H₉O; epoxy, —CR(—O—)CR₂; hydroxy; carbamate, —NR(C=O)OR; urethane, —O(C=O)NRR; univalent ureido —NR(C=O)NR₂; silyl, —Si(R²)$_a$(OR³)$_{3-a}$; where R², R³ and a are as defined; silylalkyl, —C₆H₉(C₂H₄Si(R²)$_a$(OR³)$_{3-a}$)₂, where a is as defined, wherein C₆H₉ refers to cyclohexyl; and univalent isocyanurato (—N)(NR)(NR)C₃O₃, where each occurrence of R is independently selected from the group consisting of hydrogen, alkyl of from 1 to about 6 carbon atoms, cycloalkyl of from 3 to about 10 carbon atoms, alkenyl of from 2 to about 6 carbon atoms, arylene of from 6 to about 10 carbon atoms or alkarylene of from 7 to about 12 carbon atoms.

In another embodiment herein the set of divalent organofunctional groups herein includes, but is not limited to, carbamate, —(-)N(C=O)OR; ureido —NR(C=O)NR—; and divalent isocyanurato, (—N)₂(NR)C₃O₃ where R is independently selected from the group of hydrogen, alkyl of from 1 to about 6 carbon atoms, cycloalkyl of from 3 to about 10 carbon atoms, alkenyl of from 2 to about 6 carbon atoms, arylene of from 6 to about 10 or alkarylene from 7 to about 12 carbon atoms.

In yet another embodiment herein, the set of trivalent organofunctional groups herein includes, but is not limited to, carbamate, (-)₂NC(=O)O—; ureido, (-)₂NC(=O)NR—, and trivalent isocyanurato (—N)₃C₃O₃, wherein each occurrence of R is independently selected from the group consisting of hydrogen, alkyl of from 1 to about 6 carbon atoms, cycloalkyl of from 3 to about 10 carbon atoms, alkenyl of from 2 to about 6 carbon atoms, arylene of 6 to about 10 carbon atoms, or alkarylene of 7 to about 12 carbon atoms.

In a further embodiment herein, the set of tetravalent organofunctional groups herein includes, but is not limited to ureido, (-)₂N(C=O)N(-)₂.

In a specific embodiment the organofunctional silane is univalent ureido —NR(C=O)NR₂, divalent ureido —NR(C=O)NR— and (-)₂N(C=O)NR₂; trivalent ureido (-)₂NC(=O)NR—; tetravalent ureido (-)₂N(C=O)N(-)₂ and trivalent isocyanurato (—N)₃C₃O₃ where R is independently selected from the group of hydrogen, alkyl of from 1 to about 6 carbon atoms, cycloalkyl of from 3 to about 10 carbon atoms, alkenyl of from 2 to about 6 carbon atoms, arylene of from 6 to about 10 or alkarylene from 7 to about 12 carbon atoms.

In a specific embodiment r is an integer of from 1 to 4 and specifically from 2 to 4, and more specifically 3 to 4.

In one embodiment organofunctional silane (a) is an ureidoalkoxysilane such as the non-limiting example of ureidoalkoxysilane (a) described herein. In one more specific embodiment herein, as to the ureido silane (such as the non-limiting example of ureidoalkoxysilane (a) described herein) materials that are present and can be used, these include ureido silanes as set forth in Formula (II).

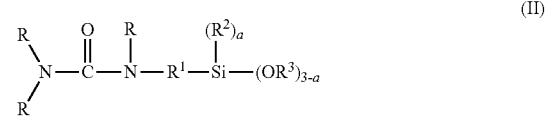

(II)

wherein each occurrence of R independently is hydrogen, alkyl of from 1 to 6 carbon atoms, cycloalkyl of from 3 to about 6 carbon atoms, alkenyl of from 2 to about 6 carbon atoms, arylene of from 6 to about 10 carbon atoms or alkarylene of from 7 to about 12 carbon atoms, and specifically the R which is bound to the nitrogen atom that is a bridge between the carbonyl and R¹, is individually selected from the group consisting of hydrogen, methyl, ethyl, propyl, iso-propyl, butyl, iso-butyl, sec-butyl, tert-butyl, and cyclohexyl; R¹ is a divalent substituted or unsubstituted aliphatic or aromatic group of up to 12 carbon atoms, specifically R¹ is selected from the members of the group consisting of an alkylene of from 1 to about 10 carbon atoms, alkenylene of from 2 to about 6 carbon atoms, arylene of from 6 to about 10 carbon atoms and alkylarylene of from 7 to about 12 carbon atoms; and more specifically, R¹ is independently methylene, ethylene, propylene, 2-methylpropylene or 2,2-dimethylbutylene; each R² independently is a monovalent hydrocarbon group of from 1 to about 10 carbon atoms, even more specifically 1 to about 6 carbon atoms, and yet even more specifically such as the non-limiting examples of alkyl, aryl and aralkyl groups such as the non-limiting examples of methyl, ethyl, butyl, hexyl, phenyl, or benzyl, more specifically, the lower alkyls of from 1 to about 4 carbon atoms and most specifically methyl; and each R³ is independently chosen from the group consisting of hydrogen, linear or branched alkyl, linear or branched alkoxy-substituted alkyl, linear or branched acyl of up to about 16 carbon atoms, specifically R³ is individually chosen from the group consisting of hydrogen, ethyl, methyl, propyl, iso-propyl, butyl, iso-butyl, sec-butyl and acetyl; and in one embodiment, at least one R³ is other than hydrogen or acetyl; and a is 0, 1 or 2.

In one specific embodiment, it will be understood herein that as used herein, the term "substituted" aliphatic or aromatic means an aliphatic or aromatic group wherein the carbon backbone may have a heteroatom located within the backbone, or a heteroatom attached to the carbon backbone, or a heteroatom containing group attached to the carbon backbone. In one embodiment some non-limiting examples of a heteroatom are oxygen, nitrogen or combinations thereof.

In one other more specific embodiment herein, ureido silane (such as the non-limiting example of ureidoalkoxysilane) employed in this disclosure is γ-ureidopropyltrimethoxysilane such as one having the structure (III):

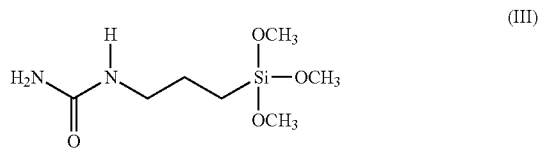 [SMILES: CO[Si](CCCNC(N)=O)(OC)OC]

which can also be used to prepare the hydrolyzate(s) and/or partial or complete condensate thereof, which can be used in the compositions and methods described herein In another specific embodiment one non-limiting example of ureido silane herein can be 3-ureidopropyltriethoxysilane which can also be used to prepare the hydrolyzates and/or partial or complete condensate thereof, which can be used in the compositions and methods described herein. Pure 3-ureidopropyltriethoxysilane is a waxy solid material. A solvent or means of solubilizing the solid material is needed for it to be useful. In one specific embodiment herein, commercially available 3-ureidopropyltriethoxysilane is dissolved in the non-limiting example of methanol, and as a result, it is not a pure compound but contains both methoxy and ethoxy groups attached to the same silicon atom. In one embodiment commercially available 3-ureidopropyltriethoxysilane is dissolved in methanol so that methanol makes up 50 weight percent solution of the solution of ureidopropyltrialkoxysilane and methanol. In another specific embodiment herein, when fully hydrolyzed, the identity of the silanes would be identical.

In one embodiment herein organofunctional silane (a) is selected from the group consisting of vinylmethyldiethoxysilane, vinyltrimethoxysilane, vinyldimethylethoxysilane, vinyltriethoxysilane, vinyltripropoxysilane, vinyl-tris(2-methoxyethoxysilane), styrylethyltrimethoxysilane, gamma-acryloxypropyltrimethoxysilane, gamma-(acryloxypropyl)methyldimethoxysilane, gamma-methacryloxypropyltrimethoxysilane, gamma-methacryloxypropyltriethoxysilane, gamma-methacryloxypropylmethyldimethoxysilane, gamma-methacryloxypropylmethyldiethoxysilane, gamma-methacryloxypropyl-tris-(2-methoxyethoxy)silane, beta-(3,4-epoxycyclohexyl)ethyltrimethoxysilane, beta-(3,4-epoxycyclohexyl)ethyltriethoxysilane, gamma-glycidoxypropyltrimethoxysilane, gamma-glycidoxypropyltriethoxysilane, gamma-glycidoxypropylmethyldiethoxysilane, gamma-glycidoxypropylmethyldimethoxysilane, gamma-mercaptopropyltrimethoxysilane, gamma-mercaptopropyltriethoxysilane, gamma-thiooctanoylpropyltrimethoxysilane, gamma-thiooctanoylpropyltriethoxysilane, bis-(trimethoxysilylpropyl)tetrasulfane, bis-(triethoxysilylpropyl)disulfane, gamma-ureidopropyltrimethoxysilane, gamma-ureidopropyltriethoxysilane, gamma-ureidopropyldimethoxyethoxysilane, gamma-ureidopropylmethoxydiethoxysilane, gamma-ureidopropylmethyldimethoxysilane, gamma-ureidopropylmethyldiethoxysilane, gamma-ureidopropylmethylmethoxyethoxysilane, gamma-carbamatopropyltrimethoxysilane, gamma-carbamatopropyltriethoxysilane, isocyanurate propyltrimethoxysilane, bis-(trimethoxysilylpropyl)urea, bis-(triethoxysilylpropyl)urea, 2-cyanoethyltrimethoxysilane, 2-cyanoethyltriethoxysilane and combinations thereof.

In one specific embodiment organofunctional silane (a) is selected from the group consisting of gamma-ureidopropyltrimethoxysilane, gamma-ureidopropyltriethoxysilane, gamma-ureidopropyldimethoxyethoxysilane, gamma-ureidopropylmethoxydiethoxysilane, gamma-ureidopropylmethyldimethoxysilane, gamma-ureidopropylmethyldiethoxysilane, gamma-ureidopropylmethylmethoxyethoxysilane, N,N'-bis-(3-triethoxysilylpropyl)urea, N,N'-bis-(3-trimethoxysilylpropyl)urea, N,N'-bis-(3-diethoxymethylsilylpropyl)urea, N,N'-bis-(3-diisopropoxymethylsilylpropyl)urea, N,N-bis-(3-triethoxysilylpropyl)urea, N,N-bis-(3-trimethoxysilylpropyl)urea, N,N-bis-(3-diethoxymethylsilylpropyl)urea, N,N-bis-(3-diisopropoxymethylsilylpropyl)urea, N,N,N'-tris-(3-triethoxysilylpropyl)urea, N,N,N'-tris-(3-trimethoxysilylpropyl)urea, N,N,N'-tris-(3-diethoxymethylsilylpropyl)urea, N,N,N'-tris-(3-diisopropoxysilylpropyl)urea, N,N,N,'N'-tetrakis-(3-triethoxysilylpropyl)urea, N,N,N,'N'-tetrakis-(3-trimethoxysilylpropyl)urea, N,N,N,'N'-tetrakis-(3-diethoxymethylsilylpropyl)urea, N,N,N,'N'-tetrakis-(3-diisopropoxymethylsilylpropyl)urea, tris-(3-trimethoxysilylpropyl)isocyanurate, and combinations thereof.

In one specific embodiment organofunctional silane (a) is selected from the group consisting of gamma-ureidopropyltrimethoxysilane, gamma-ureidopropyltriethoxysilane, gamma-ureidopropyldimethoxyethoxysilane, gamma-ureidopropylmethoxydiethoxysilane, gamma-ureidopropylmethyldimethoxysilane, gamma-ureidopropylmethyldiethoxysilane, gamma-ureidopropylmethylmethoxyethoxysilane and combinations thereof.

In one other embodiment herein the stable suspension herein can be substantially free of hazardous air pollutant. The phrase "substantially free of hazardous air pollutant" (HAP or HAPs) is a level of HAP that is present after a removal of HAP from the aqueous solution of hydrolyzate or partial and/or complete condensate of organofunctional silane described above, more specifically a removal that results in a lower level of HAP compared to an equivalent aqueous solution of hydrolyzate or partial and/or complete condensate of organofunctional silane that has not had HAP removed. In one specific embodiment, such a removal of HAP can be accomplished through sparging with an inert gas such as the non-limiting example of nitrogen. In one more specific embodiment such sparging can be conducted for a period of from about 2 to about 96 hours, more specifically of from about 4 to about 72 hours, even more specifically of from about 6 to about 48 hours and most specifically of from about 8 to about 24 hours. In another embodiment herein some other techniques that can be used herein for the removal of HAP are reduced pressure and/or distillation.

In one even more specific embodiment hazardous air pollutants comprise a level of HAPs of specifically less than about 1 weight percent, more specifically less than about 0.2 weight percent, even more specifically less than about 0.05 weight percent and most specifically less than about 0.01 weight percent, said weight percents being based on the total weight of the detectable composition.

In one specific embodiment herein HAPs are any compounds used in paints that have been identified as HAPs in the Clean Air Act Amendments of 1990 of the United States of America. In one specific embodiment HAPs can be byproducts formed from the hydrolysis of organofunctional silane (a) described above. In one specific embodiment HAPs includes acetamide, acrylamide, acrylic acid, acrylonitrile, allyl chloride, aniline, benzene, 1,3-butadiene, caprolactam, catechol, cumene, 1,2-dichloroethane, dichloroethyl ether, diethanolamine, dimethylamino-azobenzene, dimethylfomamide, dimethylphthalate, epichlorohydrin, ethyl acrylate, ethyl benzene, ethylene dibromide, ethylenimine, formaldehyde, hexachlorbenzene, n-hexane, hydroquinone, isophorone, maleic anhydride, methanol, methyl ethyl ketone, methyl isobutyl ketone, methylene chloride, naphthalene, nitrobenzene, 2-nitropropane, pentachlorophenol, phenol, propylene oxide, styrene, 1,1,2,2-tetrachloroethane, toluene, 2,4-toluene diisocyanate, 1,1,1-trichloroethane, trichloroethylene, 2,4,6-trichlorophenol, vinyl acetate, vinyl chloride, xylenes, m-xylene, o-xylene, p-xylene and combinations thereof. An example is the release of methanol from the hydrolysis of gamma-ureidopropyltrimethoxysilane.

In another specific embodiment in addition to being substantially free of HAPs or containing levels of HAPs of specifically less than about 1 weight percent, more specifically less than about 0.2 weight percent, even more specifically less than about 0.05 weight percent and most specifically less than about 0.01 weight percent, said weight percents being based on the total weight of the detectable composition, the detectable composition herein can further be low in volatile organic compound (VOC). In one specific embodiment VOC can be byproducts formed from the hydrolysis of organofunctional silane (a) described above. In one more specific embodiment VOC is any organic compound which participates in any atmospheric photochemical reactions; that is any organic compound other than those, which the Environmental Protection Agency of the United States of America (EPA) designates as having negligible photochemical reactivity. In a more specific embodiment VOC can be selected from the group consisting of methanol, ethanol, n-propanol, 2-propanol, n-butanol, 2-butanol, tert-butanol and combinations thereof. In a further embodiment herein, low in VOC is a level of VOC of specifically less than about 10 weight percent, more specifically less than about 5 weight percent, even more specifically less than about 2 weight percent and most specifically less than about 1 weight percent, said weight percents being based on the total weight of the composition.

In the application of coatings, such as in the application of coatings to metal surfaces, VOC is calculated according EPA Method 24 from percent non-volatile, with corrections on exempt solvents and water. The non-volatile content is measured based on ASTM Standards D2369 and D3960. In one embodiment, generally, a weighed sample of material is placed in a weighed dish and placed in a convection oven at 110° C. for 1 hour. The weight remaining in the dish is then determined. The amount of VOC can then be calculated by subtracting the weight remaining in the dish from the sum of the weight of sample and the weight of the dish. The percent VOC is calculated by dividing the remainder of the weight determined above by the weight of the sample and multiplying the quotient by 100%. In one embodiment, glycols which are more specific to applications, which exhibit low VOC besides the others described herein are 1,4-cyclohexanedimethanol, trimethylolpropane, glycerol, pentaerythritol and combinations thereof.

In one embodiment herein the colloidal metal oxide, (b) is selected from the group consisting of aluminum oxide, cerium oxide, silica, titania, zirconium oxide and combinations thereof. The silica can be a silica sol material such as aqueous colloidal silica, specifically with acidic pH. Some non-limiting examples of silica sol materials are those that may be purchased from Cabot Corporation and from other suppliers such as Wacker Chemie, Degussa, Nissan Chemical, and Nalco Chemical Company. One specific non-limiting example of an effective silica sol, Cab-O-Sperse A205, is an aqueous dispersion of high purity fumed silica in deionized water available from Cabot Corporation. Cab-O-Sperse A205 has a pH of about 5-7, a solids content of about 12%, a viscosity of less than 100 centipoise (cPs) and a specific gravity of about 1.07. In one embodiment herein a colloidal metal oxide (b) is understood to include silica. In one embodiment colloidal metal oxide (b) is cerium oxide.

In one embodiment herein, cerium oxide can be cerium oxide sols which are commercially available. In one specific embodiment cerium oxide sols that are commercially available, comprise cerium oxide particles in aqueous colloidal suspension. In one more specific embodiment herein some non-limiting commercially available cerium oxide sols that may be mentioned as exemplary include colloidal cerium oxide nitrate and cerium oxide acetate, both available from Rhodia and as well as those cerium oxide sols available from Nyacol Nano Technologies Inc. In one more specific embodiment herein, cerium oxide acetate sol includes 20 weight percent cerium oxide particles. In yet another specific embodiment, some non-limiting exemplary cerium oxide sols includes those having particle sizes of less than about 100 nanometers (nm), more specifically less than about 50 nm and most specifically less than about 20 nm. In another specific embodiment some non-limiting exemplary pHs of cerium oxide sols, are those having pH values of on the order of from 1 to about 9, more specifically, of from 1 to about 6 and most specifically of from 2 to about 4. In yet a more specific embodiment some other non-limiting examples of other metal oxides, e.g., metal oxide sols, include those such as ZnO, $ZrO_2$, $TiO_2$, $Al_2O_3$ and combinations thereof.

In one more specific embodiment the stable suspension comprising colloidal metal oxide (c) can comprise colloidal metal oxide in an amount of specifically of from about 0.001 to about 36 weight percent, more specifically of from about 0.01 to about 30 weight percent, and most specifically of from about 0.1 to about 20 weight percent, said weight percents being based on the total weight of the stable suspension. In yet another embodiment herein, colloidal metal oxide can further comprise silica, and more specifically silica sol.

In one embodiment herein, a more specific colloidal cerium oxide may be sourced from Nyacol Nano Technologies, and has the following characteristics:

| | $CeO_2$ ACT |
|---|---|
| $CeO_2$ (wt. %) | 20 |
| Particle Size (nm) | 10-20 |
| Particle Charge | Positive |
| pH | 3.0 |
| Specific Gravity | 1.22 |
| Viscosity | 10 |
| Counter Ion (mol/mol) | 0.4 Acetate |

Further, the water soluble organic dye (c) is such that it will not interfere with the coating composition, e.g., will not form precipitates or result in gelation of the suspension at 25° C. temperature for a period of at least about 48 hours, more specifically, for a period of about 48 hours to at least about 18 months. In one embodiment, the water soluble organic dye (c) will not result in destabilization of the colloidal metal oxide aqueous colloidal suspension (e.g., cerium oxide aqueous colloidal suspension) i.e., it is a stable suspension. In one embodiment, the water soluble organic dye (c) is such that it has an acetate counterion. In another embodiment herein the water soluble organic dye (c) is stable, i.e., the definition of stable given for stable suspension herein applies here as well, and the water soluble organic dye is such that it does not result in precipitation of the colloidal metal oxide (c) in the detectable composition.

In one specific embodiment, the water soluble organic dye (c) has a positive charge and counterion derived from a carboxylic acid containing from 1 to about 6 carbon atoms, more specifically from 1 to about 3 carbon atoms, such as the non-limiting examples of formic acid, acetic acid and the like.

In one non-limiting embodiment, the water soluble organic dye (c) has the general formulae (IV):

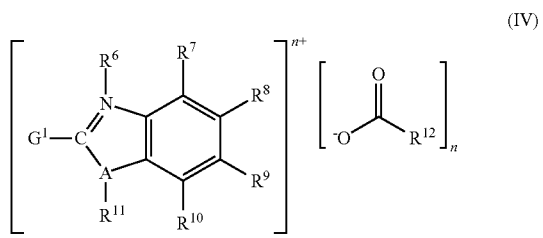

wherein:
- $G^1$ is an organic group having from 1 to about 20 carbon atoms and containing at least one oxygen or nitrogen heteroatom;
- A is a nitrogen atom or $(-)_3C-R^*$, where $R^*$ is a monovalent group chosen from alkyl, cycloalkyl, alkenyl, aralkyl or aryl group having up to about 10 carbon atoms;
- $R^6$ is an alkyl, a hydroxylalkyl, an alkoxyalkyl, a cycloalkyl, an aralkyl optionally substituted with a halogen or alkoxy group, an aryl optionally substituted with a halogen or alkoxy group, a cyanoalkyl, a carbamatoalkyl or a carboalkoxyalkyl group containing up to about 10 carbon atoms, or hydrogen;
- $R^7$ is an alkyl, alkoxy, aryl alkylsulfonyl, or arylsulfonyl group containing up to about 10 carbon atoms or hydrogen;
- $R^8$ is an alkyl, alkoxy, aryl alkylsulfonyl, arylsulfonyl, or aminosulfonyl group containing up to about 10 carbon atoms or hydrogen;
- $R^9$ is an alkyl, alkoxy, aryl alkylsulfonyl, or arylsulfonyl group containing up to about 10 carbon atoms or hydrogen;
- $R^{10}$ is an alkyl, alkoxy, aryl alkylsulfonyl, or arylsulfonyl group containing up to about 10 carbon atoms or hydrogen;
- $R^{11}$ is an alkyl, a hydroxylalkyl, an alkoxyalkyl, cycloalkyl, an aralkyl optionally substituted with a halogen or alkoxy group, an aryl optionally substituted with a halogen or alkoxy group, a cyanoalkyl, a carbamatoalkyl or an alkoxycarbonylalkyl group containing up to about 10 carbon atoms or hydrogen;
- $R^{12}$ is an alkyl group containing from 1 to about 6 carbon atoms or hydrogen; and
- n is an integer of from 1 to 3, more specifically 1 or 2, and most specifically 1.

In one embodiment, $G^1$ is a monovalent organic group of the general formula (V):

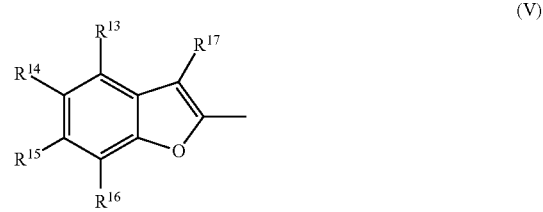

wherein:
- $R^{13}$ is an alkyl or alkoxy group containing from 1 to about 6 carbon atoms, halogen, hydrogen or together with $R^{14}$ forms a fused aryl group containing up to 16 carbon atoms, or a ring containing a $-O-CH_2-O-$ group or $-O-CH_2CH_2-O-$ group bonded to the aromatic ring of the structure (V) which contains up to 16 carbon atoms;
- $R^{14}$ is an alkyl or alkoxy group containing from 1 to 6 carbon atoms, hydrogen, halogen, carboxyl, carboalkoxy, aminocarbonyl, carbamato, sulfonyl, alkylsulfonyl, aminosulfonyl or together with $R^{13}$ or $R^{15}$ forms a fused aryl group containing up to about 16 carbon atoms, or a ring containing a $-O-CH_2-O-$ group or $-O-CH_2CH_2-O-$ group bonded to the aromatic ring of the structure (V) which contains up to 16 carbon atoms;
- $R^{15}$ is an alkyl or alkoxy group of from 1 to about 6 carbon atoms, a halogen or a hydrogen or together with $R^{14}$ or $R^{16}$ forms a fused aryl group containing up to about 16 carbon atoms, or together with $R^{14}$ or $R^{16}$ forms a fused ring containing a $-O-CH_2-O-$ group or $-O-CH_2CH_2-O-$ group bonded to the aromatic ring of the structure (V) which contains up to about 16 carbon atoms, or a monovalent group of from 2 to about 12 carbon atoms derived from 2H-[1,2,3]triazole;
- $R^{16}$ is an alkyl or alkoxy group of from 1 to about 6 carbon atoms, a halogen or hydrogen or together with $R^{15}$ forms a fused aryl group containing up to 16 carbon atoms, or a ring containing a $-O-CH_2-O-$ group or $-O-CH_2CH_2-O-$ group bonded to the aromatic ring of the structure (V) which contains up to 16 carbon atoms; and
- $R^{17}$ is an alkyl group of from 1 to about 6 carbon atoms, hydrogen, or a phenyl group which is optionally substituted with an alkyl or alkoxy group of up to about 8 carbon atoms.

In another embodiment, $G^1$ is a monovalent organic group of the general formula (VI):

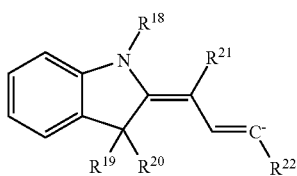

(VI)

wherein:
each $R^{18}$, $R^{19}$, $R^{20}$, $R^{21}$ and $R^{22}$ is independently an alkyl group of from 1 to about 6 carbon atoms or hydrogen.

In one embodiment, the water soluble organic dye of chemical formula (IV) has A equal to —CR* and $G^1$ is the group of formula (VI).

In another embodiment, the water soluble organic dye of chemical formula (IV) has A equal to —CR* and $G^1$ is the group of formula (VI), where $R^{18}$, $R^{19}$ and $R^{20}$ are each methyl and $R^{21}$ and $R^{22}$ are each hydrogen.

In another embodiment, the water soluble organic dye of chemical formula (IV) has A is a nitrogen atom and $G^1$ is the group of formula (V).

In another non-limiting embodiment, the water soluble organic dye (c) has the general formulae (VII):

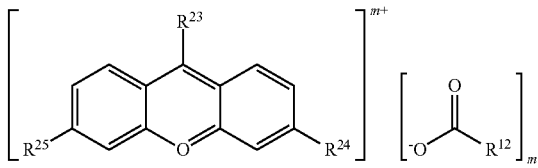

(VII)

wherein:
$R^{12}$ is an alkyl group containing from 1 to about 6 carbon atoms or hydrogen;

$R^{23}$ is hydrogen, an alkyl group of from 1 to about 6 carbon atoms, an aryl group of from 6 to about 10 carbon atoms, an aralkyl group of from 7 to about 12 carbon atoms or an aryl group of from 6 to about 12 carbon atoms substituted with a hydroxycarbonyl group (—C(=O)OH) or an alkoxycarbonyl group (—C(=O)$OR^{26}$), where $R^{26}$ is an alkyl group of from 1 to about 4 carbon atoms;

$R^{24}$ is hydrogen, an alkyl group containing 1 to about 6 carbon atoms, hydroxyl or amino having the structure —$NR^{27}R^{28}$, where $R^{27}$ and $R^{28}$ are each independently a hydrogen or alkyl group of from 1 to about 6 carbon atoms;

$R^{25}$ is hydrogen, an alkyl group containing 1 to about 6 carbon atoms, hydroxyl or amino having the structure —$NR^{27}R^{28}$, where $R^{27}$ and $R^{28}$ are each independently a hydrogen or alkyl group of from 1 to about 6 carbon atoms; and m is an integer from 1 to 3, more specially 1 or 2, and most specifically 1.

In still another embodiment, the water soluble organic dye of formula (VII) has $R^{24}$ and $R^{25}$ equal to —$NR^{27}R^{28}$, where each $R^{27}$ and $R^{28}$ is independently a hydrogen or an alkyl group of from 1 to about 3 carbon atoms and $R^{23}$ is $C_6H_4$—$CO_2H$.

In one further embodiment herein the water soluble organic dye (c) is derived from xanthenylium, 1H-benzoimidazole, 3H-indole, 2-allylidene-2,3-dihydro-1H-indole and/or benzofuran.

The water soluble organic dye (c) used herein can be selected from the group consisting of Amezine Rhodamine B Liquid, Amezine Brilliant R Red P Liquid, Amewhite BAC Liquid and combinations thereof.

The water soluble organic dye (c) used herein can be a fluorescing dye or merely a visible dye. It will be understood that a fluorescing dye may still be visible to the naked eye, but a visible dye will be such that it does not contain fluorescing components.

If the water soluble organic dye (c) is a visible dye, it is such that it may have a characteristic color under visible light which is visibly detectable by eye in a coating of the desired thickness on a substrate. This would allow a qualitative determination of whether the coating is present on the substrate along with the ability to quantify the thickness of the coating according to the methods of the invention herein.

If the water soluble organic dye (c) is a fluorescing dye, it will be such that it produces a detectable fluorescence even when small amounts of the dye are used in the stable suspension or where the stable suspension (the coating composition) is very thin. The wavelength of light which causes the dye to fluoresce should be different from (i.e., must not overlap with) the wavelength of light emitted from the dye when it fluoresces. This ensures that there is no undue interference with the measurement of the intensity of the fluorescence by the light used to cause the dye to fluoresce.

In one embodiment the stable suspension can further comprise water specifically deionized water.

In one embodiment the detectable composition herein can exhibit a period of stability which is at least about twice, more specifically at least about 3 times, and most specifically at least about 5 times that of an equivalent composition in which soluble organic dye (c) is replaced with a water soluble organic dye which is other than the water soluble organic dye (c). In one embodiment herein the detectable composition can have a period of stability of specifically for at least about 48 hours, more specifically from about 48 hours to about 5 years, even more specifically from about 72 hours to about 3 years, still even more specifically of from about 96 hours to about 2 years, and most specifically of from about 1 week to about 18 months, at a temperature of 25° C.

In another specific embodiment, in addition to the organofunctional silane and/or hydrolyzate and/or partial or complete condensate thereof (a), colloidal metal oxide (b), water soluble organic dye (c) and water (d) of the detectable composition described herein, the shelf-life of the combination can be markedly improved by the addition of a stabilizing agent thereto. In one specific embodiment, with the addition of certain stabilizers, the shelf life of the detectable composition can be extended.

In one other embodiment herein the phrase "stabilizing agent" as used herein shall be understood to be a substance which is (1) soluble in water, (2) not a hazardous air pollutant and optionally additionally not a VOC and (3) retards precipitation or gelation of the silane (a), and/or hydrolyzate and/or condensate thereof.

In another embodiment herein the solubility of the stabilizing agent in water is such that there is at least no visible phase separation resulting from the formation of at least two distinct layers of the stabilizing agent and the aqueous composition and that stabilizing agent is able to retard precipitation or gelation in the composition as a result of using the specific stabilizing agent at the specifically used amount. In a more specific embodiment the stabilizing agent can have a solubility in water of specifically from complete miscibility to about 1 weight percent, more specifically from about 50 to about 2 weight percent and most specifically from about 30 to about 1 weight percent, said weight percents being based on the total weight of the composition.

In yet an even further embodiment herein the retardation of the precipitation or gelation of the silane (a), hydrolyzate and/or condensate thereof can comprise eliminating any visible precipitation or gelation for a period of time from the composition as compared to an equivalent composition except for said stabilizing agent that would have said precipitation or gelation within the same time period.

In another specific embodiment, a host of stabilizing agents may be mentioned as exemplary. In one embodiment herein, some non-limiting examples of stabilizing agents include, for example alcohols, glycols, triols, polyols, glycol ethers, esters, ketones, pyrrolidones, or polyethersilanes and combinations thereof, provided that polyethersilane is different from organofunctional silane (a); and as indicated above, provided that stabilizing agent is limited to materials that are not HAPs.

In one embodiment polyether silane is of the general formula $R^6O(EO)_m$—$[CH_2]_n$—Si—$(OR)_3$ where m is 1 to about 20, n is 1 to about 12 and R and $R^6$ are each independently a linear, branched or cyclic organic group of 1 to about 16 carbon atoms, more specifically of 1 to about 12 carbon atoms and most specifically of 1 to about 8 carbon atoms and EO is an oxyethlyene group.

In a more specific embodiment the above described polyether silane is at least one of the general formulae $R^6O(EO)_{7.5}$—$CH_2$—$CH_2$—$CH_2$—Si—$(OMe)_3$, or $R^6O$ $(EO)_3$—$CH_2$—$CH_2$—$CH_2$—Si—$(OMe)_3$ where (EO) is as defined, $R^6$ is methyl and (OMe) is a methoxy group. In another embodiment herein any one or more of the herein described stabilizers (stabilizing agents) can be used in any of the compositions and/or methods described herein.

In a more specific embodiment herein, some non-limiting examples of specific stabilizers include wherein stabilizing agent is selected from the group consisting of ethanol, 1-propanol, 2-propanol, 2-methyl-1-propanol, 2-methyl-2-propanol, 1-butanol, 2-butanol, 2-methyl-1-butanol, 2-methyl-2-butanol, 2,2-dimethyl-1-propanol, 1-pentanol, 2-pentanol, 4-methyl-2-pentanol, propylene glycol, 1,3-butanediol, 1,4-butane diol, 2-methyl-1,3-propanediol, 2-methyl-2,4-pentanediol, tetraethylene glycol, poly(ethylene glycol), dipropylene glycol, tripropylene glycol, poly (propylene glycol), 1,5-pentanediol, esterdiol 204, 2,2,4-trimethylpentanediol, 2-ethyl-1,3-hexanediol, glycerol, trimethyolpropane, trimethylolpropane allyl ether, glycerol ethoxylate, glycerol ethoxylate-co-propoxylate triol, glycerol propoxylate, pentaerythritol, 1-methoxy-2-propanol (propylene glycol methyl ether), 1-ethoxy-2-propanol, 1-propoxy-2-propanol, 1-butoxy-2-propanol, 2-butoxyethanol, di(propylene glycol)butyl ether, poly(propylene glycol) monobutyl ether, di(propylene glycol)dimethylether, methyl acetate, ethyl acetate, ethyl lactate, 2-methoxyethyl acetate, 2-butoxyethyl acetate, propylene glycol methyl ether acetate, propylene glycol ethyl ether acetate, acetone, methyl ethyl ketone, diacetone alcohol, $MeO(EO)_{7.5}$—$CH_2$—$CH_2$—$CH_2$—Si—$(OMe)_3$ wherein MeO is methoxy and (EO) is as defined above; and combinations thereof.

In another specific embodiment, the stabilizing agent when used in a stability-increasing amount provides for a period of stability for said detectable composition which is at least two times that of an equivalent composition having no added stabilizing agent. In a further more specific embodiment the stabilizing agent provides a period of stability for said composition, which is at least three times that of an equivalent composition having no added stabilizing agent. In a most specific embodiment the stabilizing agent provides a period of stability for said composition, which is at least five times that of an equivalent composition having no added stabilizing agent. In one more specific embodiment the stabilizing agent provides for a period of stability of the composition of specifically a least about 48 hours, more specifically from about 48 hours to about 5 years, still more specifically from about 72 hours to about 3 years, even more specifically of from about 96 hours to about 2 years, and most specifically of from about 1 week to about 18 months at room temperature.

In another embodiment the phrase "a stability increasing amount" as pertains to the stabilizing agent, shall be understood to be an amount of stabilizing agent that provides for the periods of stability defined above. In a more specific embodiment, "a stability-increasing amount" shall be understood to be an amount of stabilizing agent that provides for the retarding of precipitation or gelation of the condensate in a detectable composition as described herein, compared to an equivalent composition that utilizes less than such an amount of the same stabilizing agent. It will be understood that a stability-increasing amount will vary widely depending on factors such as the stabilizing agent, the hydrolyzable alkoxysilane and other composition components as described herein. In one embodiment herein, it will be understood herein that a stability-increasing amount is any additional amount beyond any amount of stabilizing agent that may be generated in the hydrolysis of organofunctional silane and will increase the stability of the aqueous solution of partial and/or complete condensate of organofunctional silane.

In another embodiment herein the detectable compositions described herein are substantially free of chromium and/or phosphate. In one specific embodiment herein, the compositions described herein can have a high flashpoint. In a further specific embodiment high flashpoint can comprise a flashpoint of at least about 21 degrees Celsius, more specifically greater than about 25 degrees Celsius and most specifically greater than about 30 degrees Celsius. In one embodiment herein, high flash point can comprise a flashpoint of from about 24 to about 50 degrees Celsius, more specifically from about 24 to about 38 degrees Celsius and most specifically from about 30 to about 38 degrees Celsius. The flash point is determined in accordance ASTM D93-13e1, Standard Test Methods for Pensky-Martens Closed-Cup Tester.

In another specific embodiment herein, additionally, as an optional adjuvant to the above components, the stable suspension (composition) and methods described herein may include a $C_1$-$C_4$ alkoxy silane compound to provide Si—O bonds in the working solutions. In another specific embodiment herein, such Si—O bonds can comprise Si—O—Si bonds with the adjuvant and the silanes(s) described herein. In another specific embodiment herein, the compositions and methods described herein may include at least one $C_1$-$C_4$ alkoxy silane compound and more specifically at least two $C_1$-$C_4$ alkoxy silane compounds.

In one more specific embodiment, these adjuvant compounds can be represented by the formula (VIII)

wherein $R^{29}$ is a monovalent hydrocarbon group having from 1 to about 10 carbon atoms, more specifically from 1 to about 8 carbon atoms and most specifically from 1 to about 4 carbon atoms, or $OR^{33}$ and each $R^{33}$ is independently chosen from $C_1$-$C_4$ alkyl. In one even more specific embodiment herein some non-limiting examples of formula (VIII) can be at present, tetraethylorthosilicate (TEOS) or methyltriethoxysilane can be mentioned.

In one embodiment herein, these compounds of formula (VIII) and others encompassed by the formula will hydrolyze in solution (such as aqueous solution) to provide a source of Si—O bonds. In one other embodiment herein the detectable composition and method(s) herein can further comprise water specifically in addition to any water present in aqueous cerium oxide sol described herein.

In one embodiment herein, the detectable composition described herein can contain organofunctional silane (a) and/or hydrolyzate and/or partial or complete condensate thereof in an amount of specifically from about 0.01 to about 80 weight percent, more specifically of from about 0.1 to about 60 weight percent and most specifically of from about 1 to about 40 weight percent; colloidal metal oxide (b) in an amount of specifically from about 0.001 to about 36 weight percent, more specifically of from about 0.01 to about 25 weight percent and most specifically of from about 0.1 to about 20 weight percent; water soluble organic dye (c) in an amount of from about 0.0001 to about 5 weight percent, more specifically from about 0.0005 to about 2 weight percent, and most specifically from about 0.001 to about 1 weight percent; and water (d) in an amount of from about 20 to about 99.99 weight percent, more specifically from about 40 to about 99.9 weight percent, and most specifically from about 60 to about 98.9 weight percent; optional stabilizing agent in an amount of specifically from about 1 to about 50 weight percent, more specifically of from about 2 to about 40 weight percent and most specifically of from about 3 to about 30 weight percent; and, optionally an adjuvant in an amount of specifically from about 0.01 to about 15 weight percent, more specifically from about 0.1 to about 10 weight percent and most specifically from about 0.1 to about 5 weight percent, all of said weight percents being based on the total weight of the detectable composition. It will be understood herein that the respective amounts of components (a), (b), (c) and (d), and any optional components used in the detectable composition will total 100 weight percent and amounts of the above stated ranges will be adjusted if necessary to achieve the same. In another embodiment the methods described herein can use the same composition amounts described above for the composition.

In one more specific embodiment, some non-limiting examples of exemplary detectable compositions are those which are substantially chromate and/or specifically substantially phosphate free and include
(a) from about 0.01 to about 80 weight percent, more specifically from about 0.1 to about 70 weight percent and most specifically from about 3 to about 60 weight percent ureido silane or hydrolyzate and or partial or complete condensate forms thereof;
(b) from about 0.001 to about 36 weight percent, more specifically from about 0.01 to about 25 weight percent and most specifically from about 0.1 to about 20 weight percent colloidal metal oxide;
(c) from about 0.0001 to about 5 weight percent, more specifically from about 0.0005 to about 2 weight percent, and most specifically from about 0.001 to about 1 weight percent water soluble organic dye (c) such as Amezine Rhodamine B Liquid, Amezine Brilliant R Red P Liquid and Amewhite BAC Liquid;
(d) from about 20 to about 99.99 weight percent, more specifically from about 40 to about 99.9 weight percent, and most specifically from about 60 to about 98.9 weight percent water;
(e) optional stabilization additive (agent) percent in an amount of up to about 25 weight percent, more specifically from about 0.1 to about 20 weight percent and most specifically from about 1 to about 15 weight percent;
(f) optional $C_1$-$C_4$ alkoxy silane compound or hydrolyzate thereof in an amount of up to about 25 weight percent, more specifically from about 0.01 to about 20 weight percent and most specifically from about 1 to about 15 weight percent; and
(g) optionally minimum amounts of pH adjustment agents, said minimum amounts of pH adjustment agents being specifically from about 0.001 to about 1.2 weight percent, more specifically from about 0.01 to about 1.0 weight percent and most specifically from about 0.01 to about 0.6 weight percent; said weight percents are based on the total weight of the aqueous sol composition.

In one embodiment herein the detectable composition is a coating composition consisting essentially of:
(a) at least one ureido silane having the structure:

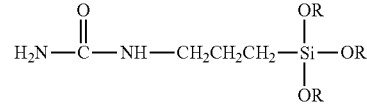

wherein R is independently hydrogen or alkyl of from 1 to about 4 carbon atoms, or condensate compounds therefrom in the amount of from about 0.01 to about 80 weight percent;
(b) cerium oxide particles in the amount of from about 0.001 to about 36 weight percent;
(c) water soluble organic dye in an amount of from about 0.001 to about 2 weight percent; and,
(d) water in an amount of the remainder of the weight of the coating composition
wherein the weight of the ureido silane is the sum of the weights of each ureido silane component and the weight percents are based upon the total weight of the coating composition.

In a most specific embodiment herein there are provided detectable compositions having the following range (in weight percent) of the components:
(a) from about 3 to about 60 weight percent ureido silane or hydrolyzate form thereof;
(b) from about 0.001 to about 10 weight percent Si and/or Ce oxide particles;
(c) from about 0.001 to about 1 weight percent water soluble organic dye (c) such as Amezine Rhodamine B Liquid, Amezine Brilliant R Red P Liquid and Amewhite BAC Liquid;
(d) from about 38 to about 94 weight percent water;
(e) from about 1 to about 15 weight percent stabilizing agent; and
(f) from about 1 to about 15 weight percent adjuvant, the remainder being minor amounts of pH regulating (adjustment) agents, wherein minor amounts is equivalent to minimum amounts described above for pH adjustment agents. In one embodiment herein the herein-described compositions having components in the noted weight percent amounts are present in such weight percent amounts based on the total combined weight percent of the compositions (e.g., 100 weight percent).

In a further embodiment, there is provided herein a detectable composition consisting essentially of
(a) at least one ureido silane having the structure:

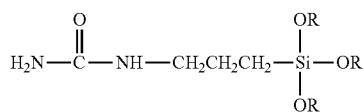

wherein R is independently hydrogen or an alkyl of from 1 to about 4 carbon atoms, or condensate compounds therefrom in the amount of from about 0.01 to about 80 weight percent;
(b) cerium oxide particles in the amount of from about 0.001 to about 36 weight percent;
(c) water soluble organic dye in an amount of from about 0.001 to about 1 weight percent and having the structure of formula (IV) or (VII);
(d) water in an amount of the remainder of the weight of the composition; and
(e) stabilizing agent in the amount of about 1 to about 20 weight percent, wherein the weight of the ureido silane is the sum of the weights of each ureido silane component and the percent by weight is based upon the total weight of the composition.

In one embodiment herein the herein-described compositions having components in the noted weight percent amounts are present in such weight percent amounts based on the total combined weight percent of the compositions (e.g., 100 weight percent).

In another embodiment herein, hazardous air pollutants (HAPS) such as the non-limiting example of MeOH are removed from the mixing process (method) in which the ureido silane, and (aqueous) cerium sol are first mixed. In another embodiment, after removal of substantial amount of the MeOH or other volatiles formed via this mixing, stabilizing agents and optionally water, are added to the reaction mixture to enhance product stability. In one specific embodiment, the stabilizing agents, especially those with a boiling point above that of water, can also be added before the removal of MeOH and/or other volatiles. Methanol is a hazardous air pollutant (HAP) and volatile organic compound (VOC).

In one embodiment herein there is also provided a detectable coating composition comprising:
(1) organofunctional silane and/or hydrolyzate and/or partial or complete condensate thereof;
(2) water soluble organic dye having a positive charge and a counterion derived from a carboxylic acid containing from 1 to about 6 carbon atoms; and,
(3) water,
wherein said composition does not contain detrimental amounts of precipitates for a period of at least 48 hours when stored at 25° C. It will be understood herein that all of the choices described herein for the detectable composition, silane component (a), water soluble dye (c) and water (d), optional stabilizing agent, optional adjuvant, optional pH adjustment agents, method(s), coated substrate, and any other description provided herein also applies equally to the detectable coating composition in the absence of colloidal oxide component (b).

In one specific embodiment herein, at present some non-limiting exemplary methods disclosed herein, comprise contacting the desired metal surface with an aqueous sol comprising: (a) a ureido silane compound, (b) Si and/or Ce oxide particles, and (c) a water soluble organic dye. In another specific embodiment and as stated above, the sol may include a stabilizing agent and the optional adjuvant.

In another embodiment herein the coating compositions and/or methods described herein can be used to provide a coating, e.g. a conversion or passivation coating, for metals such as steel and aluminum and zinc-coated steel, wherein said coating improves adhesion to further coatings thereon such as the non-limiting example of paint, and likewise provides improved corrosion protection to said metals. In yet another embodiment, metals treated by the compositions and/or methods herein can be used in commercial and industrial applications of coated metal sheets such as sheet metal used in construction and cold-rolled steel, and the like. The shape of the substrate can be in the form of a sheet, plate, bar, rod or any shape desired.

There is provided herein a method of determining the uniformity of a detectable composition applied to a substrate comprising:
(i) applying to a surface of a substrate a detectable composition comprising:
(a) organofunctional silane and/or hydrolyzate and/or partial or complete condensate thereof;
(b) colloidal metal oxide;
(c) water soluble organic dye having a positive charge and a counterion derived from a carboxylic acid containing from 1 to about 6 carbon atoms; and,
(d) water, wherein said composition does not contain detrimental amounts of precipitates for a period of at least 48 hours when stored at 25° C.; and,
(ii) measuring an optical property of the applied coating, the resulting measurement being related to the uniformity of the applied coating.

In the present invention, the detectable composition is prepared by the method comprising:
(i) adding the organofunctional silane and/or hydrolyzate and/or partial or complete condensate thereof (a) to water (d) and mixing the admixture to form an aqueous solution;
(ii) hydrolyzing and partially or completely condensing the organofunctional silane (a) of step (i);
(iii) adding the colloidal metal oxide (b) to step (ii);
(iv) adding the water soluble organic dye having a positive charge and a counterion derived from a carboxylic acid containing from 1 to about 6 carbon atoms (c) to either step (ii) or step (iii); and optionally
(v) adding a stabilizing agent to any of the steps (i) to (iv).

In one embodiment, the pH of the detectable composition is specifically of from about 3 to about 9, more specifically of from about 4 to about 6.

In the present invention, a detectable composition, such as the pretreatment coating, is deposited (e.g., coated) upon at least a portion of the outer surface of the metal substrate. The entire outer surface of the metal substrate is coated with the detectable composition, such as the pretreatment.

There is provided herein a metal substrate coated with a composition comprising:
(a) organofunctional silane or hydrolyzate and/or partial or complete condensate thereof;
(b) colloidal metal oxide;

(c) water soluble organic dye having a positive charge and a counterion derived from a carboxylic acid containing from 1 to about 6 carbon atoms; and, (d) water, wherein said composition does not contain detrimental amounts of precipitates for a period of at least 48 hours when stored at 25° C.

The detectable composition may be applied to the surface of the metal substrate by any conventional application technique, such as spraying, immersion or roll coating in a batch or continuous process. The temperature of the detectable composition at application is typically from about 10° C. to about 85° C., and preferably from about 15° C. to about 60° C.

Continuous processes are typically used in the coil coating industry and also for mill application. The detectable composition can be applied by any of these conventional processes. For example, in the coil industry, the substrate is cleaned and rinsed and then usually contacted with the treating solution by roll coating with a chemical coater. The treated strip is then dried by heating and painted and baked by conventional coil coating processes.

Mill application of the treating solution can be by immersion, spray or roll coating applied to the freshly manufactured metal strip. Excess detectable composition is typically removed by wringer rolls. After the detectable composition has been applied to the metal surface, the metal is dried at room temperature or at elevated temperatures to remove the water and promote the condensation reactions of the components with themselves and with the surface to form the dried and cured detectable composition on the surface of the substrate. Alternately, the treated substrate can be heated at from about 65° C. to about 125° C. for 2 to about 60 seconds to produce a coated substrate having a dried residue of the detectable composition, such as a pretreatment coating, thereon. If the substrate is already heated from the hot melt production process, no post application heating of the treated substrate is required to facilitate drying. The temperature and time for drying the detectable composition will depend upon such variables as the percentage of components (a), (b), (c) and optionally (d) in the detectable composition and type of substrate.

If the substrate is a metal substrate, before depositing the coatings upon the surface of the metal substrate, foreign matter is typically removed from the metal surface by thoroughly cleaning and degreasing the surface. The surface can be cleaned by physical means, such as by mechanical abrasion, or by chemical means, such as by cleaning/degreasing the surface with commercially available alkaline or acidic cleaning agents, such as sodium metasilicate and sodium hydroxide. A non-limiting example of a cleaning agent is CHEMKEEN 163, a phosphate cleaner, which is commercially available from PPG Industries, Inc. of Pittsburgh, Pa. Following the cleaning step, the metal substrate is usually rinsed with water, specifically deionized water, in order to remove any residue. The metal substrate can be air dried using an air knife, by flashing off the water by brief exposure of the substrate to a high temperature, or by passing the substrate between squeegee rolls.

In yet another specific embodiment herein, the detectable composition described herein is applied to the treated metal surface to result in a detectable composition weight of equal to or greater than about 0.5 milligram per square foot (5 mg per square meter) of the treated surface, more specifically applied to the treated metal surface with a weight of from about 0.5 to about 500 milligrams per square foot (about 5 to about 5,400 mg per square meter) being more specific weight of from about 3 to about 300 milligrams per square foot (about 32 to about 3,200 mg per square meter).

After the detectable composition is applied on the substrate it can be dried and/or cured at room temperature or by exposure to heat, using methods known by those skilled in the art.

The measuring of the optical property can be conducted following coating of the substrate with the detectable composition or after the detectable composition is dried and/or cured.

In one embodiment, the measuring of the optical property is by visual observation or by instrument, such as by colorimeter or a fluorometer. It will be understood herein that the expression "optical property", as used herein, is the visibility by the naked eye or by an instrument of the presence of color, or absence thereof, on at least a portion of a substrate coated by the detectable composition described herein.

If visual observation is used, the water soluble organic dye (c) can be a colored dye that imparts a color in the visible range of the electromagnetic radiation spectrum or a fluorescent dye that is excited with an external radiation source, such as an ultraviolet lamp or visible lamp. The human eye is able to differentiate between different intensities of color. The eye scanning the surface of the substrate treated with the detectable composition can determine non-uniformity in the color or areas on the substrate that contain or do not contain any detectable composition, because these areas have or do not have the color of the colored dye, or fluoresce or do not fluoresce when excited.

If a quantitative determination is needed, a calibration procedure is performed in order to correlate the measured visible intensity of the color with the weight/thickness of the detectable composition containing the colored dye component. At least 3 calibration standards are produced with known detectable composition weights or thicknesses representative of the range of the detectable composition weights or thicknesses that are desirable. It is preferred that a more statistically significant eight calibration standard samples are utilized, including 2 samples of blank substrate, two samples representative of target detectable composition weight/thickness, two samples representative of low detectable composition weight/thickness and two samples representative of high detectable composition weight or thickness. These calibration standards may be prepared using coating methods known to one skilled in the art. The color intensity is determined by taking these standards of various color intensity and comparing them to the sample of the substrate containing the detectable composition, using visual observation to match the color intensity of the sample substrate with the standards of known weight/thickness. Once the match is made, the weight/thickness is determined by referencing the amount of weight/thickness used to prepare the standard. The detectable composition weight for each calibration standards can be verified independently using any appropriate method known by one skilled in the art. A preferred independent method would be the use of XRF (X-ray) fluorescence spectrometers, which measure the elements on the surface of the substrate. Illustrative of the method, substrates coated with varying amounts of the detectable composition and dried can be analyzed using an XRF (X-ray) fluorescence spectrometer, as for example, an Oxford Twin-X bench top XRF spectrometer with a Focus-5+ detector, tube voltage of 4 kV, tube current of 750 uA, and measuring time of 5 minutes. The peak area, expressed in counts per second, is interpolated on a calibration curve of a set of previously measured standards. The standards can be prepared by coating methods which deposit a very precise amount of detectable composition on the surface of a substrate, such as spin coating or draw-down bars.

The uniformity of the detectable composition can determined using the method of colored standards and observing different portions (areas) of the treated substrate. A mask, such as a sheet of material with a hole can be used to focus the visual observation to a specific known area, and then to compare the intensity of the color with the standards. The mask prevents bias that the surrounding colored area of the treated substrate might introduce into the observation. In addition, the uniformity as a function of the area being observed can also be determined by varying the size of the hole in the mask. The uniformity can then be assessed relative to the size of the area of the mask. In complex shapes, this method allows for an unbiased determination of the detectable composition weight/thickness at corners, on flat surfaces, which may vary due to the different wetting out and wicking of the detectable composition.

If a fluorometer is used, the water soluble organic dye (c) will be a fluorescent dye distributed in the detectable composition. Visual observation, where the detector is the human eye, can also be used to detect a water soluble fluorescent organic dye (c), provide, provided that the dye is excited with an external radiation source, such as an ultraviolet or visible lamp.

The fluorescence can be measured by methods known in the art. Typically, a detection station includes a light source for emitting light onto the detectable composition of a wavelength and intensity sufficient to cause the fluorescent component of the detectable composition to fluoresce at detectable levels and a detector which collects light produced by the fluorescence of the fluorescent component of the detectable composition and converts the collected light into an analog or digital signal indicative of the intensity of the fluorescence of the coating. The light source and the detector can be housed together in a probe head.

The light source emits electromagnetic radiation in the ultraviolet and/or visible spectral regions. A preferred light source is a mercury vapor lamp filtered optically such that only those emissions lines between 250 and 400 nm are incident upon an illuminated sample. Alternative light sources include, but are not limited to xenon lamps, deuterium lamps, hollow cathode lamps, tungsten lamps, ion lasers, solid state lasers, diode lasers and light emitting diodes. It is preferred that the energy or energy range of the light source used is coincident with that of one or more electronic absorption bands of the fluorescing agent incorporated into the sample, but not coincident with that of the fluorescence emission of the same fluorescing agent.

The detector collects light produced by the fluorescence of the fluorescent component of the detectable composition and converts the collected light into an analog or digital electrical signal indicative of the intensity of the fluorescence of the coating. The detector contains optics for the collection and spectral filtering of light that is reflected by and emitted by a sample following illumination with light from the aforementioned light source. It is preferred, but not essential, that the spectral filtering optics reject light of energy or energy range coincident with that of the light source, while transferring, to the optical fiber, light of energy or energy range coincident with the fluorescence emission of the fluorescing agent in the sample. This light of energy or energy range coincident with the fluorescence emission of the fluorescing dye in the sample can be conveyed via optical fiber to the main detector unit. The detector unit can comprise any means known to one skilled in the art to isolate and measure electromagnetic radiation of an energy or energy range coincident with that of the fluorescence emission of the fluorescing agent in the sample. One embodiment of the main detector unit is a spectrograph comprising a single monochromator with a photodiode array. The light exiting the optical fiber enters the monochromator and is dispersed by energy using a grating and then is imaged onto the photodiode array to produce an electrical signal.

The signal is passed to a computing device, such as a general purpose or dedicated computer, which converts the signal into a reading of the thickness of the detectable composition based upon a pre-determined relationship between the fluorescence intensity of the detectable composition and the thickness and weight of the detectable composition. The signal is first converted to a measurement of the fluorescence intensity of the detectable composition. The thickness of the detectable composition is then determined by entering the measurement of the fluorescence intensity into a formula describing the predetermined mathematical relationship between the thickness and weight of the detectable composition and fluorescence intensity of the detectable composition. Optionally, the computing device may be connected to an alarm device which is activated when the thickness of the detectable composition falls outside of a critical range.

Because the detectable composition may be applied, and the fluorescence of the detectable composition may be measured at different times during the manufacture of the item, the application (coating) station and the detecting station need not be sequential in a manufacturing line, or even in the same building or geographical location. For example, a metal roll or sheet can be coated in a mill and the thickness of the detectable composition can be determined immediately following the application of the detectable composition, or shortly thereafter following a drying or curing step.

A coating station can be provided after the detection station for application of additional detectable composition if the initial thickness of the detectable composition falls below a desired critical thickness. This station would be inactive during normal operations, but can be activated manually or automatically when the detectable composition thickness falls below a critical thickness. The amount of detectable composition applied by this second coating station can be variable to prevent over-coating of the substrate, resulting in a detectable composition which is too thick. The thickness of the detectable composition applied by the second coating station can be controlled automatically by reference to the thickness of the initially applied detectable composition on the substrate previously measured at the detection station. Typically, the activation of this station would be automatic and the activation would coincide with an alarm to notify operators of the line of the insufficient operation of the first coating station.

Alternatively, depending upon the nature of the coating and the logistics of the manufacturing process, the determination of the detectable composition thickness can be made well after the coating step, and with many intervening steps. For instance, the metal can be slit, cut, shaped, stamped, welded or otherwise processed before the thickness of the detectable composition is determined. In many instances, this is desirable in order to ascertain whether the detectable composition remains on the manufactured item in a thickness sufficient to protect the underlying metal substrate. For example, steel strip may be manufactured and coated overseas and sold domestically to a manufacturer who processes the metal, and prior to application of a subsequent coating layer, would ascertain the thickness of the detectable composition on the metal. In any case, the detection station can be followed by the above-described second coating station to ensure that the detectable composition layer is of the desired thickness.

A calibration procedure is performed in order to correlate the measured fluorescence signal intensity with the weight/thickness of the detectable composition containing the fluorescent component. At least 3 calibration standards are produced with known detectable composition weights or thicknesses representative of the range of the detectable composition weights or thicknesses that are desirable. It is preferred that a more statistically significant eight calibration standard samples are utilized, including 2 samples of blank substrate, two samples representative of target detectable composition weight/thickness, two samples representative of low detectable composition weight/thickness and two samples representative of high detectable composition weight or thickness. These calibration standards may be prepared using coating methods known to one skilled in the art. The measured value of fluorescence intensity is determined using the measuring device (detector) described previously. The measured fluorescence intensity can be expressed as either the intensity at the energy of the maximum of the fluorescence emission spectrum, or as the area under the fluorescence emission spectrum. It is preferred, but not essential, that a statistically significant number of replicate measurements, e.g. six, are performed on each calibration standard sample. The detectable composition weight for each calibration standard sample is then verified independently using any appropriate method known by one skilled in the art. A preferred independent method would be the use of XRF (X-ray) fluorescence spectrometers, which measure the elements on the surface of the substrate. Illustrative of the method, substrates coated with varying amounts of the detectable composition and dried can be analyzed using an XRF (X-ray) fluorescence spectrometer, as for example, an Oxford Twin-X bench top XRF spectrometer with a Focus-5+ detector, tube voltage of 4 kV, tube current of 750 uA, and measuring time of 5 minutes. The peak area, expressed in counts per second, is interpolated on a calibration curve of a set of previously measured standards. The standards can be prepared by coating methods which deposit a very precise amount of detectable composition on the surface of a substrate, such as spin coating or draw-down bars. A plot of verified coating weight versus measured fluorescence intensity yields a calibration plot. A mathematical expression of the relationship between detectable composition weight or thickness and fluorescence intensity can be derived by one skilled in the art from a best fit line through the points on the plot.

If a colorimeter is used, the water soluble dye (c) is a colored dye. A colorimeter is a device the measures the absorbance of a specific wavelength of light in a detectable composition. The concentration of the colored, water soluble dye (c) in the detectable composition can then be determined using Beer-Lambert Law, which states that the concentration of the dye is proportional to the concentration of the dye. The essential parts of a colorimeter are: a light source (often an ordinary low-voltage filament lamp), an adjustable aperture, a set of colored filters, a cuvette to hold the working solution, a detector (usually a photoresistor) to measure the transmitted light and a meter to display the output from the detector. Numerous colorimeters are commercially available for measuring the color of liquid solution and dried substances, such as for example, Minolta CR-400 hand held device.

The colorimeter is placed on the surface of the treated substrate containing detectable composition and activated. The colorimeter provides an analysis of the color and the intensity of the color.

Standards of carefully prepared substrates containing known amounts of the detectable composition, as discussed above, can be used to calibrate the colorimeter.

In one specific embodiment, the method for determining the weight of the detectable coating (passivation or conversion coating) on the surface of bare or coated metal substrate comprises:

(i) preparing a series of detectable coating (passivation or conversion) at different concentrations;
(ii) coating a series of metal substrates with the detectable coating,
(iii) optionally, drying the detectable coatings under the same drying conditions that are used in the on-line coating process;
(iv) determining the amount of the detectable coating on the surface of each of the treated metal substrates and the areas that are coated and calculate the amount of detectable coating gravimetrically using the equation, $$\text{weight of detectable coating}=(w^2-w^1)/(\text{area of coated surface})$$

if only one side of the substrate is coated or $$\text{weight of detectable coating}=(w^2-w^1)/[(2)(\text{area of coated surface})]$$

if two sides of the substrate are coated;
or determine the amount of detectable coating on the metal substrate by using the XRF method where the XRF standard calibration curve was used to develop a least squared linear regression equation;
(v) measuring the a* value of the CIE L*a*b* color space using a colorimeter, such as Konica Monolta Chroma Meter CR-400 of each of the coated substrate of known detectable coating weight;
(vi) plotting the a* values versus detectable coating weight and calculating the least squares linear regression equation;
(vii) measuring the detectable coating on the bare or coated metal substrate by determining the a* value using a colorimeter;
(viii) using the equation of step (vi) to calculate the amount of the detectable coating on the bare or coated metal substrate.

The disclosure herein will now be described in conjunction with the following examples which are to be regarded as being illustrative of certain embodiments of the disclosure herein but should not be viewed to restrict the disclosure. All percents herein are weight percents based on the total weight of the detectable composition unless indicated otherwise.

EXAMPLES

To match the characteristics (positive charge, acetate counter-ion) of the cerium oxide colloid, a cationic dye stabilized with an acetate counter-ion was henceforth targeted for evaluation in a detectable composition. Dyes which do not possess these features were evaluated to demonstrate the instability of the dye.

The organofunctional silane (a) use in preparing the samples was gamma-ureidopropyltrimethoxysilane, sold by Momentive under the Tradename Silquest* A-1524 silane. The colloidal cerium oxide used in the preparation of the samples contain an aqueous dispersion of cerium oxide, 20 weight percent, with a particle size of 10 to 20 nanometers, a positive charge, pH of 3, specific gravity of 1.22 and counter ion of acetate at a level of 0.4 mole acetate per mole cerium oxide, and sold by Nyacol Nano Technologies. Water (d) was deionized water. The dyes used in the Comparative Examples are shown in Table 1.

TABLE 1

A list of commercially available dyes, the manufacture and chemical structure.

| Dye | Common Name | Structure |
| --- | --- | --- |
| Keystone Keyfluor CBS-X | Fluorescent Brightener 351 | 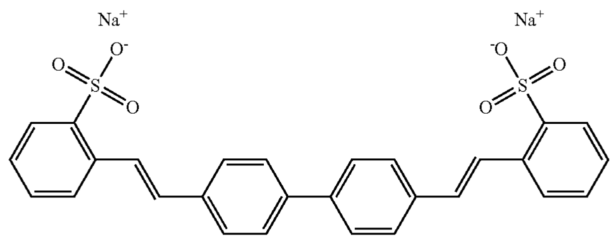 |
| Keystone Keyfluor 5BM-GX | Fluorescent Brightener 28 | 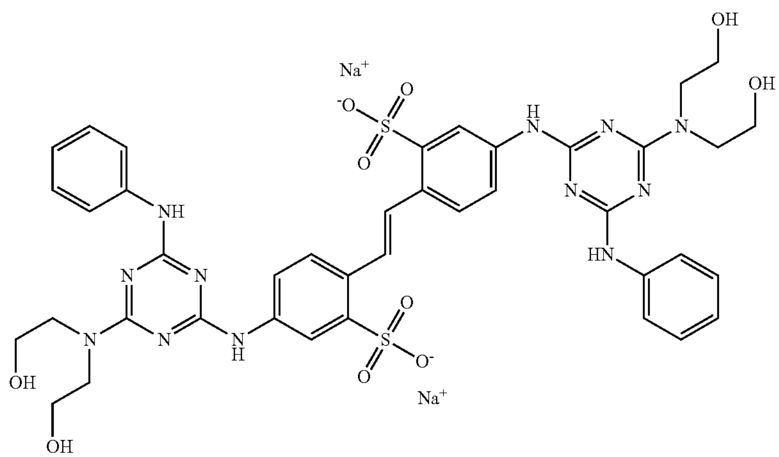 |
| Fluoroscein Sodium Salt | Uranine Acid Yellow 73 | 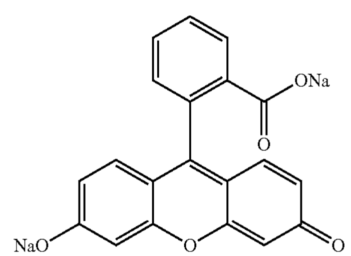 |
| Keystone Keyacid Rhodamine WT | Acid Red 388 | 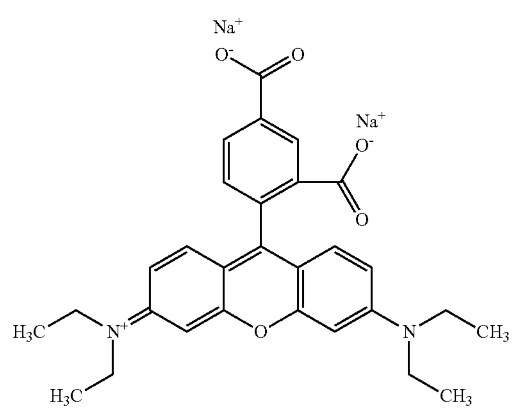 [SMILES: [Na+] ; CCN(CC)c1ccc2c(-c3ccc(C(=O)[O-])cc3C(=O)[O-])c3ccc(=[N+](CC)CC)cc-3oc2c1 ; [Na+]] |

TABLE 1-continued

A list of commercially available dyes, the manufacture and chemical structure.

| Dye | Common Name | Structure |
| --- | --- | --- |
| Keystone Keyazine Rhodamine B-EX | Basic Violet 10 | 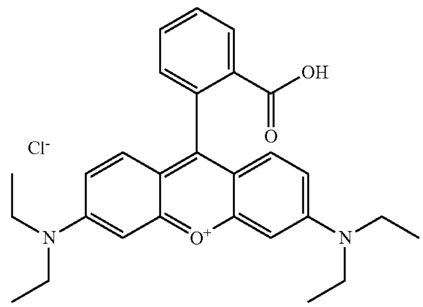 [SMILES: CCN(CC)c1ccc2c(-c3ccccc3C(=O)O)c3ccc(N(CC)CC)cc3[o+]c2c1 ; [Cl-]] |
| Keystone Pyranine 10G | Solvent Green 7 | 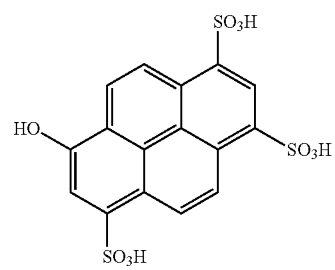 |
| BASF Basacid Blue 762 | Direct Blue 199 Cu phthalocyanine dispersion | 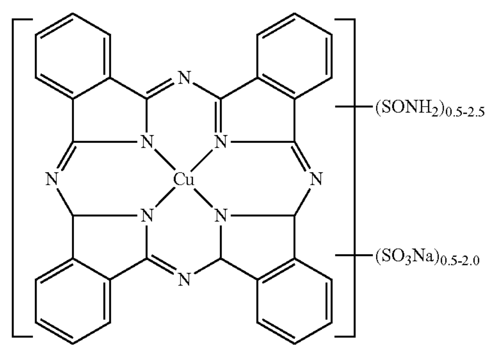 |
| BASF Puricolor Yellow AYE 23 | Acid Yellow 23 | 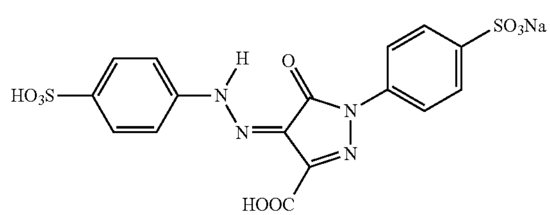 |
| Chromatech Chromatint Fluorescent Tracer 0556 | | |
| Copper Sulfate pentahydrate | $CuSO_4 \cdot 5H_2O$ | |
| BASF Lumogen F Yellow 083 | Basic Red 46, categorized as non-ionic | 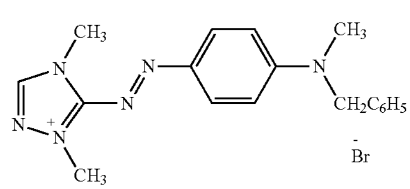 |

TABLE 1-continued
A list of commercially available dyes, the manufacture and chemical structure.
| Dye | Common Name | Structure |
| --- | --- | --- |
| Amecryl Red GRL-ED | cationic basic violet 16 | 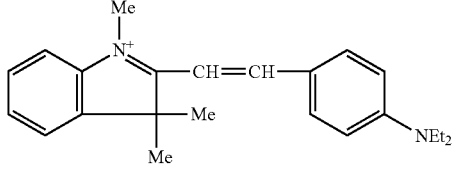 •Cl⁻ |
| Amecryl Brilliant Red 2B 200% | used for anodizing | |
| Amechrome Fiery Red ML | Direct Red 254 | |
| Keystone Keyamine Red 8BL Liquid | the composition CAS 101380-00-1 | |
| Hangzou HC Violet 2301 | violet 23 | 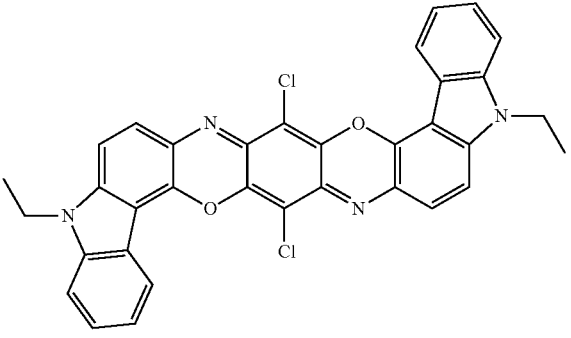 [SMILES: CCn1c2ccccc2c2c3c(ccc21)N=c1c(Cl)c2c(c(Cl)c1O3)=Nc1ccc3c(c1O2)c1ccccc1n3CC] |
| Hangzou HC Pink 8101 | Red 81 | 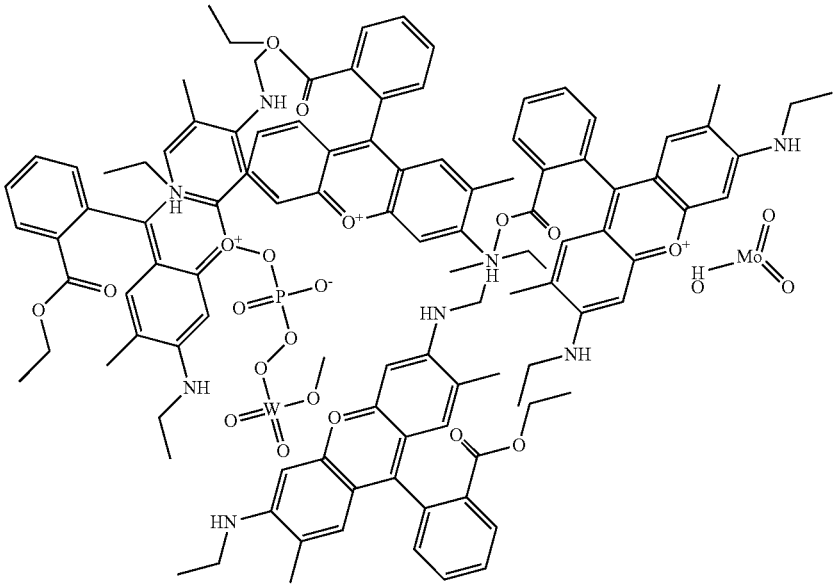 |

TABLE 1-continued

A list of commercially available dyes, the manufacture and chemical structure.

| Dye | Common Name | Structure |
| --- | --- | --- |
| Hangzou HC Rose 101 | violet 1 | 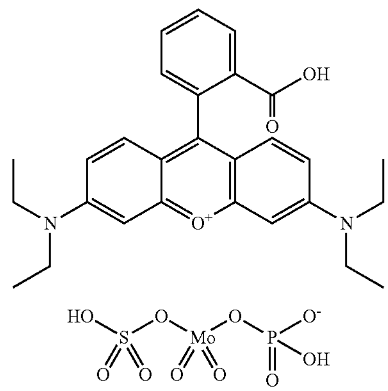 |
| Hangzou HC Yellow 101 | Yellow 1 | 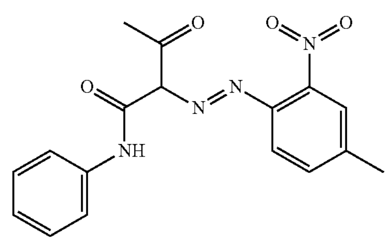 [SMILES: CC(=O)C(/N=N/c1ccc(C)cc1[N+](=O)[O-])C(=O)Nc1ccccc1] |
| Hangzou HC Blue 1501 | Blue 15:0 | 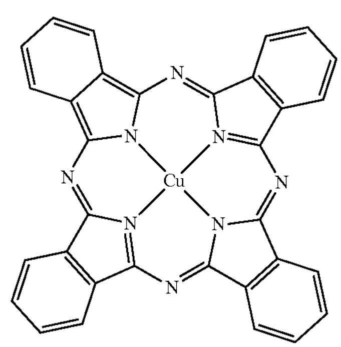 |
| Amecryl Brilliant Red 4G | Blend of Basic Red 14 (acetate) and Basic Red 14 (chloride) and chloride anion | 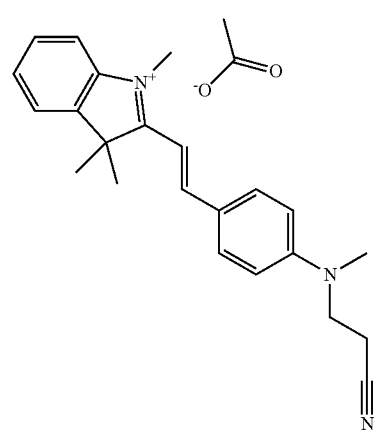 |

The dyes used in preparing Examples of the invention were:

Amezine Rhodamine B Liquid, available from American Dyestuff Corporation: Basic Violet 10 (CAS #81-88-9) dissolved in acetic acid.

Amezine Brilliant R Red P Liquid, available from American Dyestuff Corporation: Basic Red 12 (CAS #6320-14-5) in acetic acid.

Amewhite BAC Liquid, available from American Dyestuff Corporation: Optical Brightener (CAS #95078-19-6) dissolved in acetic acid.

Example 1

Detectable Composition Containing Varying Amounts of Amezine Rhodamine B Liquid Dye and 3 Weight Percent Gamma-Ureidopropyltrimethoxysilane and 1 Weight Percent Colloidal Cerium Oxide A stock solution of pretreatment was prepared by placing 3840 grams of distilled water, 120 grams of gamma-ureidopropyltrimethoxysilane and 40 grams of colloidal cerium oxide into a mixing vessel and stirring for 10 minutes at room temperature to hydrolyze and partially condense the silane. Then, to 30 grams of stock solution, 0.03 gram of 1% Amezine Rhodamine B Liquid dye was added and the appearance and stability of the detectable composition was determined. In a similar manner, admixtures of the aforementioned stock solution and varying amounts of Amezine Rhodamine B Liquid dye, where the concentrations of the dye were 0.001 gram/100 grams of detectable composition, 0.01 gram/100 grams of detectable composition, 0.1 gram/100 grams of detectable composition and 1 gram/100 grams of detectable composition. The amount of water was adjusted to give make 100 grams of detectable composition. The appearance and stability of the detectable composition were determined. The results are reported in Table 2.

Example 2

Detectable Composition Containing Varying Amounts of Amezine Rhodamine B Liquid Dye and 0.75 Weight Percent Gamma-Ureidopropyltrimethoxysilane and 0.25 Weight Percent Colloidal Cerium A stock solution of pretreatment was prepared by placing 3960 grams of distilled water, 30 grams of gamma-ureidopropyltrimethoxysilane and 10 grams of colloidal cerium oxide into a mixing vessel and stirring for 10 minutes at room temperature to hydrolyze and partially condense the silane. Then, to 30 grams of stock solution, 0.03 gram of 1% Amezine Rhodamine B Liquid dye was added and the appearance and stability of the detectable composition was determined. In a similar manner, admixtures of the aforementioned stock solution and varying amounts of Amezine Rhodamine B Liquid dye, where the concentrations of the dye were 0.001 gram/100 grams of detectable composition, 0.01 gram/100 grams of detectable composition, 0.1 gram/100 grams of detectable composition and 1 gram/100 grams of detectable composition. The amount of water was adjusted to give make 100 grams of detectable composition. The appearance and stability of the detectable composition were determined. The results are reported in Table 2.

Example 3

Detectable Composition Containing Varying Amounts of Maurine Rhodamine B Liquid Dye and 0.3 Weight Percent Gamma-Ureidopropyltrimethoxysilane and 0.1 Weight Percent Colloidal Cerium A stock solution of pretreatment was prepared by placing 3984 grams of distilled water, 12 grams of gamma-ureidopropyltrimethoxysilane and 4 grams of colloidal cerium oxide into a mixing vessel and stirring for 10 minutes at room temperature to hydrolyze and partially condense the silane. Then, to 30 grams of stock solution, 0.03 gram of 1% Amezine Rhodamine B Liquid dye was added and the appearance and stability of the detectable composition was determined. In a similar manner, admixtures of the aforementioned stock solution and varying amounts of Amezine Rhodamine B Liquid dye, where the concentrations of the dye were 0.001 gram/100 grams of detectable composition, 0.01 gram/100 grams of detectable composition, 0.1 gram/100 grams of detectable composition and 1 gram/100 grams of detectable composition. The amount of water was adjusted to give make 100 grams of detectable composition. The appearance and stability of the detectable composition were determined. The results are reported in Table 2.

Examples 4-6

Detectable Composition Containing Varying Amounts of Amezine Brilliant R Red P Dye, Gamma-Ureidopropyltrimethoxysilane and Colloidal Cerium Detectable compositions were prepared using the procedures of Examples 1 to 3, corresponding to Examples 4-6, respectively, except the dye was Amezine Brilliant R Red P. The results are reported in Table 2.

Examples 7-9

Detectable Composition Containing Varying Amounts of Amewhite BAC Liquid Dye, Gamma-Ureidopropyltrimethoxysilane and Colloidal Cerium Detectable compositions were prepared using the procedures of Examples 1 to 3, corresponding to Examples 7-9, respectively, except the dye was Amewhite BAC Liquid Dye. The results are reported in Table 2. A 365 nm lamp was used to detect the presence of these compositions.

TABLE 2

The appearance and stability of detectable compositions.

| Example | Silane concn. Weight % | Dye | Dye concn. 0.001 wt. % | Dye concn. 0.01 wt. % | Dye concn. 0.1 wt. % | Dye concn. 1 wt. % |
|---|---|---|---|---|---|---|
| 1 | 3 | Rhodamine B | Clear and stable | Clear and stable | Clear and stable | Clear and stable |
| 2 | 0.75 | Rhodamine B | Clear and stable | Clear and stable | Clear and stable | Clear and stable |
| 3 | 0.3 | Rhodamine B | Clear and stable | Clear and stable | Clear and stable | Clear and stable |
| 4 | 3 | Brilliant R Red P | Clear and stable | Clear and stable | Clear and stable | Clear and stable |
| 5 | 0.75 | Brilliant R Red P | Clear and stable | Clear and stable | Clear and stable | Clear and stable |
| 6 | 0.3 | Brilliant R Red P | Clear and stable | Clear and stable | Clear and stable | Clear and stable |
| 7 | 3 | BAC liquid | Clear and stable | Clear and stable | Clear and stable | Clear and stable |
| 8 | 0.75 | BAC liquid | Clear and stable | Clear and stable | Clear and stable | Clear and stable |
| 9 | 0.3 | BAC liquid | Clear and stable | Clear and stable | Clear and stable | Clear and stable |

Comparative Examples I-XX

Detectable Composition Containing Varying Dyes and Amounts and 3 Weight Percent Gamma-Ureidopropyltrimethoxysilane and 1 Weight Percent Colloidal Cerium The comparative Examples were prepared in a manner similar to Example 1 except that different dyes were used. The results are reported in Table 3.

The compositions of Comparative Examples I-XX are unstable and had poor appearance, such as precipitates or the inability to form a solution of the dye.

Example 10

Metal Substrates Coated with Detectable Composition Containing Amezine Rhodamine B Liquid Dye Aluminum panels, obtained from Q-Lab were used to assess the detectability of the applied compositions of these

TABLE 3

The appearance and stability of detectable compositions.

| Comparative Example | Dye | Concn. 0.01 wt. | Concn. 0.1 wt. % | Concn. wt. 1% |
|---|---|---|---|---|
| I | Keystone Keyfluor CBS-X | ppt settled | ppt settled | hazy |
| II | Keystone Keyfluor 5BM-GX | ppt settled | ppt settled | hazy |
| III | Fluoroscein Sodium Salt | settled | settled | clear |
| IV | Keystone Keyacid Rhodamine WT | | | |
| V | Keystone Keyazine Rhodamine B-EX | stable | ppt* | ppt |
| VI | Keystone Pyranine 10G | ppt | ppt | ppt |
| VII | BASF Basacid Blue 762 | stable | unstable | stable |
| VIII | BASF Puricolor Yellow AYE 23 | unstable | unstable | Stable |
| IX | Chromatech Chromatint Fluorescent Tracer 0556 | hazy | settled | more hazy |
| X | Copper Sulfate pentahydrate | hazy | settled | settled |
| XI | BASF Lumogen F Yellow 083 | not soluble | not soluble | not soluble |
| XII | Amecryl Red GRL-ED | hazy and settled | hazy | clear |
| XIII | Amercryl Brilliant Red 2B 200% | clear | settled | no data |
| XIV | Amechrome Fiery Red ML | hazy and settled | settled | opaque but not settled |
| XV | Keystone Keyamine Red 8BL Liquid | clear | ppt, settled | very hazy |
| XVI | Hangzou HC Violet 2301 | not soluble | not soluble | not soluble |
| XVII | Hangzou HC Pink 8101 | not soluble | not soluble | not soluble |
| XVIII | Hangzou HC Rose 101 | not soluble | not soluble | not soluble |
| XIX | Hangzou HC Yellow 101 | not soluble | not soluble | not soluble |
| XX | Amecryl Brilliant Red 4G | clear | slightly hazy | hazy |

It should be noted that Amezine Rhodamine B Liquid and Amezine Brilliant R Red P Liquid are chloride stabilized dyes that are dissolved in acetic acid. The concentration of the acetate/acetic acid overwhelms the concentration of the chloride (by mole, the ratio of acetate:chloride is estimated to be 7:1) in these dyes.

samples on a panel. Panels were cleaned with an alkaline cleaner and rinsed with de-mineralized water until a water break free surface was obtained. The panels were dried with air at room temperature.

The detectable composition prepared in Example 1 are applied to 2 cleaned aluminum panels by pipetting 5 grams of the composition onto the panel and removing the excess using a roller. The panel is dried at room temperature. The color of the detectable composition is observed on the panels.

Example 11

Metal Substrates Coated with Detectable Composition Containing Amezine Brilliant R Red P Aluminum panels, obtained from Q-Lab were used to assess the detectability of the applied compositions of these samples on a panel. Panels were cleaned with an alkaline cleaner and rinsed with de-mineralized water until a water break free surface was obtained. The panels were dried with air at room temperature.

The detectable composition prepared in Example 4 are applied to 2 cleaned aluminum panels by pipetting 5 grams of the composition onto the panel and removing the excess using a roller. The panel is dried at room temperature. The color of the detectable composition is observed on the panels.

Example 12

Metal Substrates Coated with Detectable Composition Containing Amewhite BAC Liquid Aluminum panels, obtained from Q-Lab were used to assess the detectability of the applied compositions of these samples on a panel. Panels were cleaned with an alkaline cleaner and rinsed with de-mineralized water until a water break free surface was obtained. The panels were dried with air at room temperature.

The detectable composition prepared in Example 7 are applied to 2 cleaned aluminum panels by pipetting 5 grams of the composition onto the panel and removing the excess using a roller. The panel is dried at room temperature. The color of the detectable composition is observed on the panels. The treated substrate is irradiated with UV radiation (365 nm) from a hand-held device, and the fluorescence of the detectable composition is observed on the panels.

Example 13

Metal Substrates Coated with Detectable Compositions Containing Rhodamine B

An aqueous stock solution was prepared by charging into a beaker water (1000 grams), a 20 weight percent solution of cerium oxide purchased from Nyacol Nao Technologies as $CeO_2$ ACT (10 grams), 3-ureidopropyltrimethoxysilane (30 grams), stirred for 15 minutes and then a dye, Rhodomine B-EX (1 gram). The stock solution was used to make serial dilutions. The stock solution (100 parts) was mixed with a silicone wetting agent having the structure, $(CH_3)_3SiCH_2CH_2Si(CH_3)_2(CH_2CH_2CH_2(OCH_2CH_2)$—$OCH_3$, where x is a number between 3 and 17 (0.1 parts) and labeled as Coating A. The stock solution (100 parts) was diluted with 100 parts of water, and then a silicone wetting agent having the structure, $(CH_3)_3SiCH_2CH_2Si(CH_3)_2(CH_2CH_2CH_2(OCH_2CH_2)_xOCH_3$, where x is a number between 3 and 17 (0.2 parts) was added to the mixture and labeled as Coating B; the stock solution (100 parts) was diluted with 100 parts of water and labeled as Coating C; the stock solution (100 parts) was diluted with 300 parts of water, and then a silicone wetting agent having the structure, $(CH_3)_3SiCH_2CH_2Si(CH_3)_2(CH_2CH_2CH_2(OCH_2CH_2)_xOCH_3$, where x is a number between 3 and 17 (0.4 parts) was added to the mixture and labeled as Coating D. The stock solution (100 parts) was diluted with water (700 parts) and then a silicone wetting agent having the structure, $(CH_3)_3SiCH_2CH_2Si(CH_3)_2(CH_2CH_2CH_2(OCH_2CH_2)_xOCH_3$, where x is a number between 3 and 17 (0.4 parts) was added to the mixture and labeled as Coating E.

Two types of metal substrates were selected for treating with the silane bath solutions. The substrates were cold rolled steel (CRS) and hot dip galvanized steel (HDG). CRS and HDG panels were obtained from ACT Laboratories. The metal substrates were cleaned by dipping in a pH 12, standard alkaline cleaning solution and rinsed with de-mineralized water until a water break free surface was obtained. The metal substrates were dried at room temperature.

The coatings A to E were applied for 5 seconds to the metal substrates, dried at 100° C. for 10 minutes. The amount of dried silane-containing coating on the surface was determined using the X-Ray Fluroescence (XRF) instrument, Oxford Twin X using a Focus-5+ detector, available from Oxford Instruments. The instrument settings were a tube current of 750 µA, a voltage of 4 kV, a peak integration from 1.35 to 2.12 keV, and an accumulation time of 60 seconds. The amounts were determined using the equations:

Amount of dried silane-containing coating $(mg/m^2)=4.59(integral,cps)+5.45(CRS$ substrate); and Amount of dried silane-containing coating $(mg/m^2)=4.52(integral,cps)+1091(HDG$ substrate) that were determined from standard calibration curves.

The XRF standards calibrations curves and equations were obtained using the procedure below. Substrates were prepared and used to construct a calibration curve. Five coating composition were prepared by mixing distilled water with 23 weight percent colloidal ceria acetate in water. The mixture was stirred for 2 minutes, and then 3-ureidopropyltrimethoxysilane was added with adequate stirring for at least 15 minutes at ambient temperature to ensure adequate hydrolysis of the silane. The resulting silane bath solution was clear and colorless and kept at ambient temperature during the coating process. The amounts of 23 weight percent colloidal ceria acetate in water, 3-ureidopropyltrimethoxysilane and water are recorded in Tables 4 and 5.

Two types of metal substrates were selected for treating with the silane bath solutions. The substrates were cold rolled steel (CRS) and hot dip galvanized steel (HDG). CRS and HDG panels were obtained from ACT Laboratories. The metal substrates were cleaned by dipping in a pH 12, standard alkaline cleaning solution and rinsed with de-mineralized water until a water break free surface was obtained. The metal substrates were dried at room temperature.

The metal substrates were weighed using an analytical balance, where the weight was recorded as $w^1$, immersed in the silane bath solution for 5 seconds, dried at 100° C. for 10 minutes and then reweighed, where the weight was recorded as $w^2$. The amount of dried silane-containing coating on the surface was calculated by subtracting $w^1$ from $w^2$, and then dividing the difference by 2 times the surface area of the metal plates that were coated. The weights were divided by 2 to take into account that both sides of the metal substrate contained the dried silane film. The amount of dried silane-containing coating is then reported as milligrams per meter squared $(mg/m^2)$.

XRF was used to detect and analyze silicon on CRS and HDG substrates, by isolating the Si peak. The instrument used in the analysis was an X-Ray Fluroescence (XRF) instrument, Oxford Twin X using a Focus-5+ detector, available from Oxford Instruments. The instrument settings were a tube current of 750 µA, a voltage of 4 kV, a peak integration from 1.35 to 2.12 keV, and an accumulation time of 60 seconds. The reported intensities, reported as cps, were the average of five measurements. The results of the reading are recorded in Tables 4 and 5.

TABLE 4

The data used to calculate the standard calibration curve using XRF method on CRS substrate.

| Amount of 3-ureido-propyltri-methoxysilane, weight percent | Amount of 23 weight percent colloidal ceria acetate, weight percent | Water weight percent | Amount of film, mg per m² | XRF integral, cps |
|---|---|---|---|---|
| 0.00 | 0.00 | 100.00 | 0 | 492.5 |
| 0.00 | 0.00 | 100.00 | 0 | 350.2 |
| 0.38 | 0.13 | 99.50 | 190 | 989.3 |
| 0.75 | 0.25 | 99.00 | 446 | 1482.8 |
| 0.75 | 0.25 | 99.00 | 356 | 1316.6 |
| 1.50 | 0.50 | 98.00 | 601 | 2600.5 |
| 1.50 | 0.50 | 98.00 | 606 | 2320.9 |
| 1.50 | 0.50 | 98.00 | 581 | 2533.9 |
| 4.50 | 1.50 | 94.00 | 1113 | 5856.5 |

TABLE 5

The data used to calculate the standard calibration curve using XRF method on HDG substrate.

| Amount of 3-ureido-propyltri-methoxysilane, weight percent | Amount of 23 weight percent colloidal ceria acetate, weight percent | Water weight percent | Amount of film, mg per m² | XRF integral, cps |
|---|---|---|---|---|
| 0.00 | 0.00 | 100.00 | 0 | 1345.3 |
| 0.00 | 0.00 | 100.00 | 0 | 1394.1 |
| 0.38 | 0.13 | 99.50 | 232 | 1920.9 |
| 0.38 | 0.13 | 99.50 | 232 | 2212.8 |
| 0.75 | 0.25 | 99.00 | 394 | 2268.8 |
| 0.75 | 0.25 | 99.00 | 394 | 2449.8 |
| 0.75 | 0.25 | 99.00 | 394 | 2706.7 |
| 0.75 | 0.25 | 99.00 | 394 | 3166.8 |
| 1.50 | 0.50 | 98.00 | 579 | 3399.3 |
| 1.50 | 0.50 | 98.00 | 579 | 3410.2 |
| 1.50 | 0.50 | 98.00 | 579 | 4275.6 |
| 1.50 | 0.50 | 98.00 | 579 | 4374.9 |
| 3.00 | 1.00 | 96.00 | 732 | 4152.4 |
| 4.50 | 1.50 | 94.00 | 1598 | 7628.3 |
| 4.50 | 1.50 | 94.00 | 1598 | 9160.9 |

A standard calibration curve using the XRF method for each metal substrate was constructed by plotting the integrals of the signal (cps) versus the amount of dried silane-containing coating (mg/m²) and calculating the least squared linear regression. The linear equation for CRS and HGD are:

Amount of dried silane-containing coating (mg/m²)=4.59(integral,cps)+5.45(CRS substrate); and Amount of dried silane-containing coating (mg/m²)=4.52(integral,cps)+1091(HDG substrate).

The data from Coating A to E are given in Table 6. The amount of the Coating A to E were determined using the XRF methods, and equations generated from the standard calibration curves.

TABLE 6

The data for the a* and XRF coating weights for Coating A to E.

| Coating | Position of substrate | Substrate CRS a* | Substrate CRS XRF amount, mg/m² | Substrate HDG a* | Substrate HDG XRF amount, mg/m² |
|---|---|---|---|---|---|
| A | Right Top | 19.23 | 1198 | 26.47 | 1050 |
| A | Right Middle | 21.47 | 1380 | 41.71 | 1714 |
| A | Right Bottom |  |  | 48.41 | 1956 |
| A | Left Top |  |  | 15.37 | 746 |
| A | Left Middle | 39.06 | 2865 |  |  |
| B | Right Top | 13.62 | 540 | 12.19 | 469 |
| B | Right Middle |  |  | 11.51 | 541 |
| B | Right Bottom | 18.82 | 1020 |  |  |
| B | Left Middle | 10.52 | 650 |  |  |
| B | Left Bottom |  |  | 32.05 | 1311 |
| C | Right Top |  |  | 19.82 | 982 |
| C | Right Bottom | 25.69 | 1400 |  |  |
| C | Left Top | 13.28 | 490 | 32.16 | 1432 |
| C | Left Middle | 15.26 | 805 |  |  |
| C | Left Bottom |  |  | 38.83 | 1763 |
| D | Right Top | 4.53 | 200 | 8.82 | 486 |
| D | Right Middle | 4.62 | 205 | 9.82 | 459 |
| D | Left Top |  |  | 5.4 | 312 |
| D | Left Bottom | 19.47 | 452 | 17.36 | 852 |
| E | Right Top | 2.22 | 102 | −0.47 | 122 |
| E | Right Middle | 2.45 | 131 | −0.58 | 121 |
| E | Left Bottom | 8.79 | 545 | 9.63 | 515 |

The values of a* were plotted against the amount of the coating on the different substrates. The plot of the a* values determined from the colorimeter for the substrate HDG is shown in FIG. 1. The data is linear, expressed by the equation:

$$a^* = 0.025X(\text{amount, mg/m}^2) - 2.78(\text{coating weight, mg/m}^2) - 2.78 \text{ correlation } r^2 = 0.987.$$

These data indicate that the coating weight can be determined quantitative over a large range of coating weights on different substrate panels and can measure non-uniformity of the coating within a single substrate panel.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A detectable coating composition comprising:
    (a) organofunctional silane and/or hydrolyzate and/or partial or complete condensate thereof;
    (b) colloidal metal oxide;
    (c) water soluble organic dye having a positive charge and a counterion derived from a carboxylic acid containing from 1 to about 6 carbon atoms and having the general formula (IV):

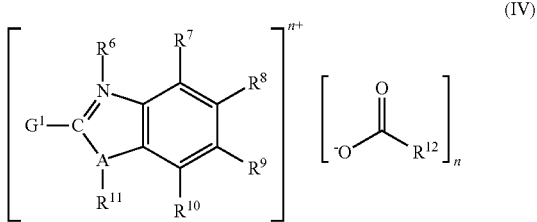

(IV)

wherein:
- $G^1$ is an organic group having from 1 to about 20 carbon atoms and containing at least one oxygen or nitrogen heteroatom;
- A is a nitrogen atom or $(-)_3C-R^*$, where $R^*$ is a monovalent group chosen from alkyl, cycloalkyl, alkenyl, aralkyl or aryl group each having up to about 10 carbon atoms;
- $R^6$ is an alkyl, a hydroxylalkyl, an alkoxyalkyl, a cycloalkyl, an aralkyl optionally substituted with a halogen or alkoxy group, an aryl optionally substituted with a halogen or alkoxy group, a cyanoalkyl, a carbamatoalkyl or a carboalkoxyalkyl group containing up to about 10 carbon atoms, or hydrogen;
- $R^7$ is an alkyl, alkoxy, aryl alkylsulfonyl, or arylsulfonyl group containing up to about 10 carbon atoms or hydrogen;
- $R^8$ is an alkyl, alkoxy, aryl alkylsulfonyl, arylsulfonyl, or aminosulfonyl group containing up to about 10 carbon atoms or hydrogen;
- $R^9$ is an alkyl, alkoxy, aryl alkylsulfonyl, or arylsulfonyl group containing up to about 10 carbon atoms or hydrogen;
- $R^{10}$ is an alkyl, alkoxy, aryl alkylsulfonyl, or arylsulfonyl group containing up to about 10 carbon atoms or hydrogen;
- $R^{11}$ is an alkyl, a hydroxylalkyl, an alkoxyalkyl, cycloalkyl, an aralkyl optionally substituted with a halogen or alkoxy group, an aryl optionally substituted with a halogen or alkoxy group, a cyanoalkyl, a carbamatoalkyl or an alkoxycarbonylalkyl group containing up to about 10 carbon atoms or hydrogen;
- $R^{12}$ is an alkyl group containing from 1 to about 6 carbon atoms or hydrogen; and
- n is an integer of from 1 to 3; and,
- (d) water, wherein said composition does not contain detrimental amounts of precipitates for a period of at least 48 hours when stored at 25° C.

2. The detectable coating composition of claim 1 wherein the organofunctional silane (a) is of the general formula (I):

(I)

wherein X
is an organofunctional group of valence r, including mono-, di-, or polyvalent groups, wherein each occurrence of $R^1$ is independently a linear, branched or cyclic divalent organic group containing up to about 12 carbon atoms, and optionally containing one or more heteroatoms, with the proviso that X and the silicon atom of the silyl group are bonded to the $R^1$ group through a covalent bond to a carbon atom of $R^1$, thereby forming a bridge between organofunctional group X and the silyl group; each occurrence of $R^2$ independently is alkyl, alkoxy-substituted alkyl, aryl, or aralkyl, all containing up to about 16 carbon atoms, each $R^3$ independently is acetyl, alkyl, or alkoxy-substituted alkyl, all containing up to about 16 carbon atoms, or hydrogen; X is an organofunctional group of valence r, including mono-, di- or polyvalent functional groups, r is an integer of from 1 to 4; and a is 0, 1 or 2.

3. The detectable coating composition of claim 2 wherein X is selected from the group consisting of: mercapto, acyloxy, glycidoxy, epoxy, epoxycyclohexyl, epoxycyclohexylethyl, hydroxy, episulfide, acrylate, methacrylate, ureido, thioureido, vinyl, allyl, thiocarbamate, dithiocarbamate, ether, thioether, disulfide, trisulfide, tetrasulfide, pentasulfide, hexasulfide, polysulfide, xanthate, trithiocarbonate, dithiocarbonate, cyanurato, isocyanurato, —NHCOOR$^5$ or —NHCOSR$^5$ where $R^5$ is a monovalent hydrocarbyl group containing from 1 to about 12 carbon atoms, or another —Si$(R^2)_a(OR^3)_{3-a}$ group wherein each $R^2$ independently is alkyl, alkoxy-substituted alkyl, aryl, or aralkyl, all containing up to about 16carbon atoms, each $R^3$ independently is acetyl, alkyl, or alkoxy-substituted alkyl, all containing up to about 16 carbon atoms, or hydrogen and a is 0, 1 or 2.

4. The detectable coating composition of claim 1 wherein the organofunctional silane (a) is of the general formula (II):

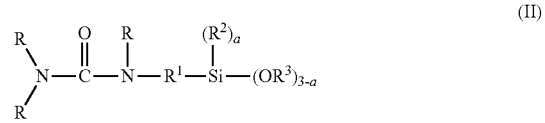

(II)

wherein each occurrence of R independently is hydrogen, alkyl of from 1 to about 6 carbon atoms, cycloalkyl of from 3 to about 6 carbon atoms, alkenyl of from 2 to about 6 carbon atoms, arylene of from 6 to about 10 carbon atoms or alkarylene of from 7 to about 12 carbon atoms; $R^1$ is a divalent substituted or unsubstituted aliphatic or aromatic group of up to about 12 carbon atoms; each $R^2$ independently is a monovalent hydrocarbon group from 1 to about 10 carbon atoms; and $R^3$ each is independently chosen from the group consisting of hydrogen, or linear or branched alkyl, linear or branched alkoxy-substituted alkyl, or linear or branched acyl each of up to about 16 carbon atoms; and a is 0, 1 or 2.

5. The detectable coating composition of claim 1 wherein the organofunctional silane (a) is selected from the group consisting of vinylmethyldiethoxysilane, vinyltrimethoxysilane, vinyldimethylethoxysilane, vinyltriethoxysilane, vinyltripropoxysilane, vinyl-tris(2-methoxyethoxysilane), styrylethyltrimethoxysilane, gamma-acryloxypropyltrimethoxysilane, gamma-(acryloxypropyl) methyldimethoxysilane, gamma-methacryloxypropyltrimethoxysilane, gamma-methacryloxypropyltriethoxysilane, gamma-methacryloxypropylmethyldimethoxysilane, gamma-methacryloxypropylmethyldiethoxysilane, gamma-methacryloxypropyl-tris-(2-methoxyethoxy)silane, beta-(3,4-epoxycyclohexyl)ethyltrimethoxysilane, beta-(3,4-epoxycyclohexyl)ethyltriethoxysilane, gamma-glycidoxypropyltrimethoxysilane, gamma-glycidoxypropyltriethoxysilane, gamma-glycidoxypropylmethyldiethoxysilane, gamma-glycidoxypropylmethyldimethoxysilane, gamma-mercaptopropyltrimethoxysilane, gamma-mercaptopropyltriethoxysilane, gamma-thiooctanoylpropyltrimethoxysilane, gamma-thiooctanoylpropyltriethoxysilane, bis-(trimethoxysilylpropyl)tetrasulfane, bis-(triethoxysilylpropyl)disulfane, gamma-ureidopropyltrimethoxysilane, gamma-ureidopropyltriethoxysilane, gamma-ureidopropyldimethoxyethoxysilane, gamma-ureidopropylmethoxydiethoxysilane, gamma-ureidopropylmethyldimethoxysilane, gamma-ureidopropylmethyldiethoxysilane, gamma-ureidopropylmethylmethoxyethoxysilane gamma-carbamatopropyltrimethoxysilane, gamma-carbamatopropyltriethoxysilane, isocyanurate propyltrimethoxysilane, bis-(trimethoxysilylpropyl)purea, bis-(trimethoxysilylpropyl)urea, 2-cyanoethyltrimethoxysilane, 2-cyanoethyltriethoxysilane and combinations thereof.

6. The detectable coating composition of claim 1 wherein $G^1$ is a monovalent organic group of the general formula (V):

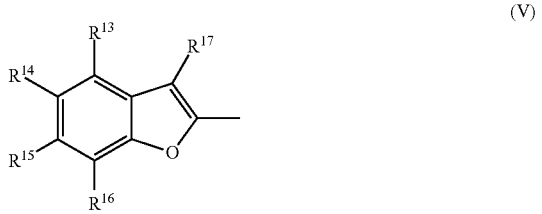

wherein:
- $R^{13}$ is an alkyl or alkoxy group containing from 1 to about 6 carbon atoms, halogen, hydrogen or together with $R^{14}$ forms a fused aryl group containing up to about 16 carbon atoms, or a ring containing a —O—CH$_2$—O— group or —O—CH$_2$CH$_2$—0— group bonded to the aromatic ring of the structure (V) which contains up to about 16 carbon atoms;
- $R^{14}$ is an alkyl or alkoxy group containing 1 to about 6 carbon atoms, hydrogen, halogen, carboxyl, carboalkoxy, aminocarbonyl, carbamato, sulfonyl, alkylsulfonyl, aminosulfonyl or together with $R^{13}$ or $R^{15}$ forms a fused aryl group containing up to about 16 carbon atoms, or a ring containing a —O—CH$_2$—O— group or —O—CH$_2$CH$_2$—O— group bonded to the aromatic ring of the structure (V) which contains up to about 16 carbon atoms;
- $R^{15}$ is an alkyl or alkoxy group of from 1 to about 6 carbon atoms, a halogen or hydrogen or together with $R^{14}$ or $R^{16}$ forms a fused aryl group of up to about 16 carbon atoms, or together with $R^{14}$ or $R^{16}$ forms a fused a ring containing a —O—CH$_2$—O— group or —CH$_2$CH$_2$—O— group bonded to the aromatic ring of the structure (V) which contains up to about 16carbon atoms, or a monovalent group of from 2 to about 12 carbon atoms derived from 2H-[1,2,3]triazole;
- $R^{16}$ is an alkyl or alkoxy group of from 1 to about 6 carbon atoms, halogen or hydrogen or together with $R^{15}$ forms a fused aryl group, or a ring containing a —O—CH$_2$—O— group or —O—CH$_2$CH$_2$—O— group bonded to the aromatic ring of the structure (V) which contains up to about 16 carbon atoms; and
- $R^{17}$ is an alkyl group of from 1 to about 6 carbon atoms, hydrogen, or a phenyl group which is optionally substituted with alkyl or alkoxy group.

7. The detectable coating composition of claim 1 wherein the $G^1$ is a monovalent organic group of the general formulae (VI):

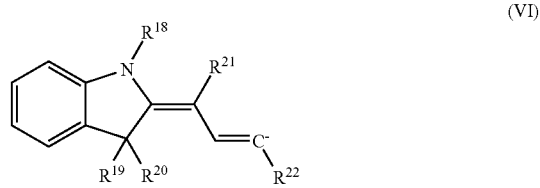

wherein:
- each $R^{18}$, $R^{19}$, $R^{20}$, $R^{21}$ and $R^{22}$ is independently an alkyl group of from 1 to about 6 carbon atoms or hydrogen.

8. The detectable coating composition of claim 7, wherein $R^{18}$, $R^{19}$ and $R^{20}$ are each methyl and $R^{21}$ and $R^{22}$ are each hydrogen.

9. The detectable coating composition of claim 1 wherein A is equal to —CR* where R* is a monovalent group selected from alkyl, cycloalkyl, alkenyl, aralkyl or aryl group having up to about 10 carbon atoms and $G^1$ is the group of the formula (VI)

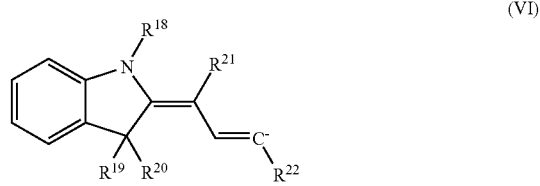

wherein:
- each $R^{18}$, $R^{19}$, $R^{20}$, $R^{21}$ and $R^{22}$ is independently an alkyl group of from 1 to about 6carbon atoms or hydrogen.

10. The detectable coating composition of claim 1, wherein A is a nitrogen atom and $G^1$ is the group of the formula (V)

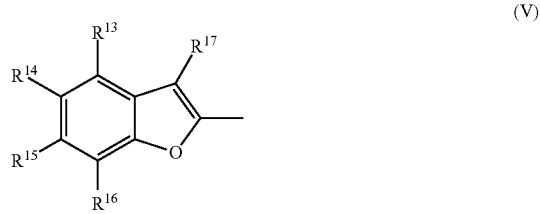

wherein:
- $R^{13}$ is an alkyl or alkoxy group containing from 1 about 6 carbon atoms, halogen, hydrogen or together with $R^{14}$ forms a fused aryl group containing up to about 16 carbon atoms, or a ring containing a —O—CH$_2$—O— group or —O—CH$_2$ 13 O— group bonded to the aromatic ring of the structure (V) which contains up to about 16 carbon atoms;

$R^{14}$ is an alkyl or alkoxy group containing 1 to 6 carbon atoms, hydrogen, halogen, carboxyl, carboalkoxy, aminocarbonyl, carbamato, sulfonyl, alkylsulfonyl, aminosulfonyl or together with $R^{13}$ or $R^{15}$ forms a fused aryl group containing uo tp about 16 carbon atoms, or a ring containing a —O—CH$_2$—O— group or —O—CH$_2$CH$_2$—O— group bonded to the aromatic ring of the structure (V) which contains up to about 16 carbon atoms;

$R^{15}$ is an alkyl or alkoxy group of from 1 to about 6 carbon atoms, a halogen or hydrogen or together with $R^{14}$ or $R^{16}$ forms a fused aryl group of up to about 16 carbon atoms, or together with $R^{14}$ or $R^{16}$ forms a fused a ring containing a —O—CH$_2$—O— group or —O—CH$_2$CH$_2$—O— group bonded to the aromatic ring of the structure (V) which contains up to about 16carbon atoms, or a monovalent group of from 2 to about 12 carbon atoms derived from 2H-[1,2,3]triazole;

$R^{16}$ is an alkyl or alkoxy group of from 1 to about 6 carbon atoms, halogen or hydrogen or together with $R^{15}$ forms a fused aryl group, or a ring containing a —O—CH$_2$—O— group or —O—CH$_2$CH$_2$—O— group bonded to the aromatic ring of the structure (V) which contains up to about 16 carbon atoms; and $R^{17}$ is an alkyl group of from 1 to about 6 carbon atoms, hydrogen, or a phenyl group which is optionally substituted with alkyl or alkoxy group.

11. The detectable coating composition of claim 1 wherein the composition consists essentially of:

a. at least one ureido silane having the structure:

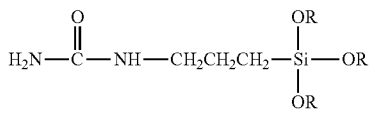

wherein R is independently hydrogen or alkyl of from 1 to about 4 carbon atoms, or condensate compounds therefrom in the amount of from about 0.01 to about 80 weight percent;

b. cerium oxide particles in the amount of from about 0.001 to about 36 weight percent;

c. water soluble organic dye in an amount of from about 0.001 to about 2 weight percent and having the general formula (IV):

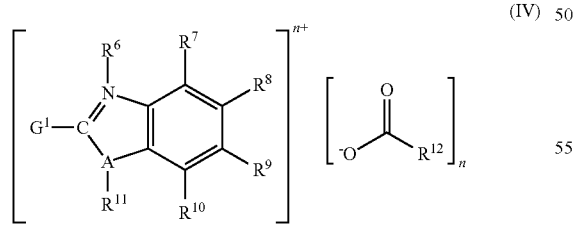

wherein:
G$^1$ is an organic group having from 1 to about 20 carbon atoms and containing at least one oxygen or nitrogen heteroatom;

A is a nitrogen atom or (-)$_3$C—R*, where R* is a monovalent group chosen from alkyl, cycloalkyl, alkenyl, aralkyl or aryl group each having up to about 10 carbon atoms;

$R^6$ is an alkyl, a hydroxylalkyl, an alkoxyalkyl, a cycloalkyl, an aralkyl optionally substituted with a halogen or alkoxy group, an aryl optionally substituted with a halogen or alkoxy group, a cyanoalkyl, a carbamatoalkyl or a carboalkoxyalkyl group containing up to about 10 carbon atoms, or hydrogen;

$R^7$ is an alkyl, alkoxy, aryl alkylsulfonyl, or arylsulfonyl group containing up to about 10carbon atoms or hydrogen;

$R^8$ is an alkyl, alkoxy, aryl alkylsulfonyl, arylsulfonyl, or aminosulfonyl group containing up to about 10 carbon atoms or hydrogen;

$R^9$ is an alkyl, alkoxy, aryl alkylsulfonyl, or arylsulfonyl group containing up to about 10carbon atoms or hydrogen;

$R^{10}$ is an alkyl, alkoxy, aryl alkylsulfonyl, or arylsulfonyl group containing up to about 10carbon atoms or hydrogen;

$R^{11}$ is an alkyl, a hydroxylalkyl, an alkoxyalkyl, cycloalkyl, an aralkyl optionally substituted with a halogen or alkoxy group, an aryl optionally substituted with a halogen or alkoxy group, a cyanoalkyl, a carbamatoalkyl or an alkoxycarbonylalkyl group containing up to about 10 carbon atoms or hydrogen;

$R^{12}$ is an alkyl group containing from 1 to about 6 carbon atoms or hydrogen; and n is an integer of from 1 to 3; and d. water in an amount of the remainder of the weight of the coating composition wherein the weight of the ureido silane is the sum of the weights of each ureido silane component and the weight percent are based upon the total weight of the coating composition.

12. The detectable coating composition of claim 1 wherein said composition consists essentially of a. at least one ureido silane having the structure:

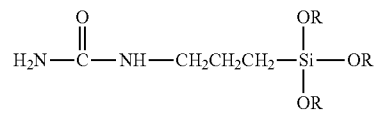

wherein R is independently hydrogen or an alkyl of from 1 to about 4 carbon atoms, or condensate compounds therefrom in the amount of from about 0.01 to about 80 weight percent;

b. cerium oxide particles in the amount of from about 0.001 to about 36 weight percent;

c. water soluble organic dye in an amount of from 0.001 to about 1 weight percent and having the structure of formula (IV)

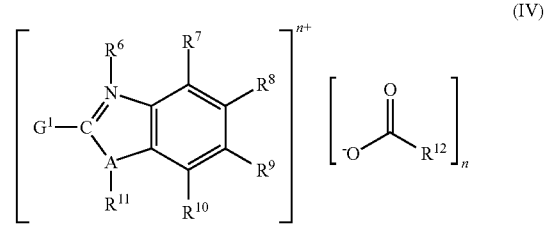

wherein:
- G¹ is an organic group having from 1 to about 20 carbon atoms and containing at least one oxygen or nitrogen heteroatom;
- A is a nitrogen atom or (−)₃C—R*, where R* is a monovalent group chosen from alkyl, cycloalkyl, alkenyl, aralkyl or aryl group each having up to about 10 carbon atoms;
- R⁶ is an alkyl, a hydroxylalkyl, an alkoxyalkyl, a cycloalkyl, an aralkyl optionally substituted with a halogen or alkoxy group, an aryl optionally substituted with a halogen or alkoxy group, a cyanoalkyl, a carbamatoalkyl or a carboalkoxyalkyl group containing up to about 10 carbon atoms, or hydrogen;
- R⁷ is an alkyl, alkoxy, aryl alkylsulfonyl, or arylsulfonyl group containing up to about 10carbon atoms or hydrogen;
- R⁸ is an alkyl, alkoxy, aryl alkylsulfonyl, arylsulfonyl, or aminosulfonyl group containing up to about 10 carbon atoms or hydrogen;
- R⁹ is an alkyl, alkoxy, aryl alkylsulfonyl, or arylsulfonyl group containing up to about 10carbon atoms or hydrogen;
- R¹⁰ is an alkyl, alkoxy, aryl alkylsulfonyl, or arylsulfonyl group containing up to about 10carbon atoms or hydrogen;
- R¹¹ is an alkyl, a hydroxylalkyl, an alkoxyalkyl, cycloalkyl, an aralkyl optionally substituted with a halogen or alkoxy group, an aryl optionally substituted with a halogen or alkoxy group, a cyanoalkyl, a carbamatoalkyl or an alkoxycarbonylalkyl group containing up to about 10 carbon atoms or hydrogen,
- R¹² is an alkyl group containing from 1 to about 6 carbon atoms or hydrogen; and
- n is an integer of from 1 to 3;
- d. water in an amount of the remainder of the weight of the composition; and
- e. stabilizing agent in the amount of about 1 to about 20 weight percent, wherein the weight of the ureido silane is the sum of the weights of each ureido silane component and the percents by weight are based upon the total weight of the composition.

13. A method for preparing the detectable coating composition of claim 1, where the method comprises:
(i) adding the organofunctional silane and/or hydrolyzate and/or partial or complete condensate thereof (a) to water (d) and mixing the admixture to form an aqueous solution;
(ii) hydrolyzing and partially or completely condensing the organofunctional silane (a) of step (i);
(iii) adding the colloidal metal oxide (b) to step (ii);
(iv) adding the water soluble organic dye having a positive charge and a counterion derived from a carboxylic acid containing from 1 to 6 carbon atoms (c) to either step (ii) or step (iii); and optionally
(v) adding a stabilizing agent to any of the steps (i) to (iv).

14. The method of claim 13, wherein the detectable coating composition is applied to the metal surface at a weight of 5 to 5,400 milligrams per square meter of the treated surface.

15. A method for determining the uniformity of a detectable coating composition of claim 1 applied to a bare or coated metal substrate comprising:
(i) applying to a surface of a substrate a detectable composition comprising:
  a. organofunctional silane and/or hydrolyzate and/or partial or complete condensate thereof;
  b. colloidal metal oxide;
  c. water soluble organic dye having a positive charge and a counterion derived from a carboxylic acid containing from 1 to about 6 carbon atoms; and,
  d. water, wherein said composition does not contain detrimental amounts of precipitates for a period of at least about 48 hours when stored at 25° C.; and,
(ii) measuring an optical property of the applied coating, the resulting measurement being related to the uniformity of the applied coating.

16. The method of claim 15, wherein the optical property is measured by visual observation or by instrument.

17. The method of claim 15, wherein the method further comprises
(i) preparing a series of detectable coating (passivation or conversion) at different concentrations;
(ii) coating a series of metal substrates with the detectable coating,
(iii) optionally, drying the detectable coatings under the same drying conditions that are used in the on-line coating process;
(iv) determining the amount of the detectable coating on the surface of each of the treated metal substrates and the areas that are coated and calculate the amount of detectable coating gravimetrically using the equation, weight of detectable coating $=(w^2-w^1)/$(area of coated surface)

if only one side of the substrate is coated or weight of detectable coating $=(w^2-w^1)/[(2)$(area of coated surface)$]$ if two sides of the substrate are coated;
or determine the amount of detectable coating on the metal substrate by using the XRF method where the XRF standard calibration curve was used to develop a least squared linear regression equation;
(v) measuring the a* value of the CIE L*a*b* color space using a colorimeter of each of the coated substrate of known detectable coating weight;
(vi) plotting the a* values versus detectable coating weight and calculating the least squares linear regression equation;
(vii) measuring the detectable coating on the bare or coated metal substrate by determining the a* value using a colorimeter;
(viii) using the equation of step (vi) to calculate the amount of the detectable coating on the bare or coated metal substrate.

18. A detectable coating composition comprising;
(a) silicon-containing compound selected from the group consisting of organofunctional silane, a hydrolyzate of said organofunctional silane, a condensate of the said organofunctional silane and mixtures thereof in the amount of 0.01 to 80 weight percent, wherein the organofunctional silane (a) is of the general formula (I):

wherein X is an organofunctional group of valence r, including mono-, di-, or polyvalent groups, wherein each occurrence of R¹ is independently a linear, branched or cyclic divalent organic group containing up to about 12 carbon atoms, and optionally containing one or more heteroatoms, with the proviso that X and the silicon atom of the silyl group are bonded to the $R^1$ group through a covalent bond to a carbon atom of $R^1$, thereby forming a bridge between organofunctional group X and the silyl group; each occurrence of $R^2$ independently is alkyl, alkoxy-substituted alkyl, aryl, or aralkyl, all containing up to about 16 carbon atoms, each $R^3$ independently is acetyl, alkyl, or alkoxy-substituted alkyl, all containing up to about 16 carbon atoms, or hydrogen; X is an organofunctional group of valence r, including mono-, di- or polyvalent functional groups, r is an integer of from 1 to 4; and a is 0, 1 or 2;

(b) water soluble organic dye having a positive charge and a counterion derived from a carboxylic acid containing from 1 to about 6 carbon atoms in an amount of from 0.0001 to about 5 weight percent and having the structure of formula (IV)

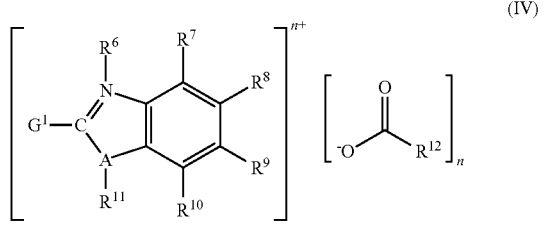

(IV)

wherein:
   $G^1$ is an organic group having from 1 to about 20 carbon atoms and containing at least one oxygen or nitrogen heteroatom;
   A is a nitrogen atom or $(-)_3C-R^*$, where $R^*$ is a monovalent group chosen from alkyl, cycloalkyl, alkenyl, aralkyl or aryl group each having up to about 10 carbon atoms;
   $R^6$ is an alkyl, a hydroxylalkyl, an alkoxyalkyl, a cycloalkyl, an aralkyl optionally substituted with a halogen or alkoxy group, an aryl optionally substituted with a halogen or alkoxy group, a cyanoalkyl, a carbamatoalkyl or a carboalkoxyalkyl group containing up to about 10 carbon atoms, or hydrogen;
   $R^7$ is an alkyl, alkoxy, aryl alkylsulfonyl, or arylsulfonyl group containing up to about 10 carbon atoms or hydrogen;
   $R^8$ is an alkyl, alkoxy, aryl alkylsulfonyl, arylsulfonyl, or aminosulfonyl group containing up to about 10 carbon atoms or hydrogen;
   $R^9$ is an alkyl, alkoxy, aryl alkylsulfonyl, or arylsulfonyl group containing up to about 10 carbon atoms or hydrogen;
   $R^1$ is an alkyl, alkoxy, aryl alkylsulfonyl, or arylsulfonyl group containing up to about 10 carbon atoms or hydrogen;
   $R^{11}$ is an alkyl, a hydroxylalkyl, an alkoxyalkyl, cycloalkyl, an aralkyl optionally substituted with a halogen or alkoxy group, an aryl optionally substituted with a halogen or alkoxy group, a cyanoalkyl, a carbamatoalkyl or an alkoxycarbonylalkyl group containing up to about 10 carbon atoms or hydrogen,
   $R^{12}$ is an alkyl group containing from 1 to about 6 carbon atoms or hydrogen;

(c) water in the amount of from 18 to 98 weight percent; and, optionally, (d) stabilizing agent in the amount of about 1 to about 20 weight percent, wherein the weight of the silicon-containing compounds is the sum of the weights of the organofunctional silane component, the hydrolyzate of said organofunctional silane component and the condensate of the said organofunctional silane and the percents by weight are based upon the total weight of the composition and wherein said composition does not contain detrimental amounts of precipitates for a period of at least 48 hours when stored at 25° C.

* * * * *